(12) United States Patent
Guckenberger et al.

(10) Patent No.: US 10,337,967 B2
(45) Date of Patent: Jul. 2, 2019

(54) MAGNETIC BASE FOR COLLECTION AND RELEASE OF PARAMAGNETIC PARTICLES

(71) Applicants: Gilson, Inc., Middleton, WI (US);
Salus Discovery LLC, Monona, WI (US)

(72) Inventors: David John Guckenberger, Oconomowoc, WI (US); Mary Christin Regier, Madison, WI (US)

(73) Assignees: SALUS DISCOVERY LLC, Monona, WI (US); GILSON, INC., Middleton, WI (US)

( * ) Notice: Subject to any disclaimer, the term of this patent is extended or adjusted under 35 U.S.C. 154(b) by 617 days.

(21) Appl. No.: 14/990,972

(22) Filed: Jan. 8, 2016

(65) Prior Publication Data
US 2017/0199107 A1    Jul. 13, 2017

(51) Int. Cl.
*G01N 35/00* (2006.01)
*G01N 1/40* (2006.01)
(Continued)

(52) U.S. Cl.
CPC ............... *G01N 1/40* (2013.01); *B01L 3/502* (2013.01); *B03C 1/32* (2013.01); *G01N 35/0098* (2013.01);
(Continued)

(58) Field of Classification Search
CPC ... B01J 19/087; B01J 19/12; B01L 2400/043; B03C 1/04; B03C 1/06; G01N 35/0098
See application file for complete search history.

(56) References Cited

U.S. PATENT DOCUMENTS

| | | |
|---|---|---|
| 3,938,961 A | 2/1976 | Lanier |
| 4,986,965 A | 1/1991 | Ushikubo |

(Continued)

FOREIGN PATENT DOCUMENTS

| | | |
|---|---|---|
| DE | 3439877 A1 | 10/1984 |
| EP | 1997557 A1 | 12/2008 |

(Continued)

OTHER PUBLICATIONS

International Search Report and Written Opinion dated Apr. 22, 2016, for International Patent Appl. No. PCT/US2016/012822, 10 pp.

(Continued)

*Primary Examiner* — Jill A Warden
*Assistant Examiner* — Dwayne K Handy
(74) *Attorney, Agent, or Firm* — Bell & Manning, LLC

(57) ABSTRACT

A magnetic base for a sample plate of a sample processing system is provided comprising a first plate comprising a first top surface; a bottom surface; and a sample plate mounting cavity wall mounted to the first top surface, wherein the first plate and the sample plate mounting cavity wall define a sample plate mounting cavity configured to accommodate a sample plate of a sample processing system. The magnetic base further comprises a second plate extending parallel to the first plate, the second plate comprising a second top surface; and a magnet mounting cavity wall extending between the bottom surface of the first plate and the second top surface of the second plate, wherein the first plate, the second plate, and the magnet mounting cavity wall define a magnet mounting cavity configured to accommodate a free floating magnet.

19 Claims, 30 Drawing Sheets

(51) Int. Cl.
*B01L 3/00* (2006.01)
*B03C 1/32* (2006.01)

(52) U.S. Cl.
CPC ... *B01L 2300/06* (2013.01); *B01L 2300/0609* (2013.01); *B01L 2300/0829* (2013.01); *B03C 2201/18* (2013.01); *G01N 2001/4038* (2013.01); *G01N 2035/00564* (2013.01)

(56) References Cited

U.S. PATENT DOCUMENTS

| | | | |
|---|---|---|---|
| 6,448,092 | B1 | 9/2002 | Tuunanen |
| 6,461,034 | B1 * | 10/2002 | Cleveland ............ B01F 7/00291 366/273 |
| 8,603,416 | B2 | 12/2013 | Beebe et al. |
| 2004/0022677 | A1 | 2/2004 | Wohlstadter |
| 2007/0148785 | A1 | 6/2007 | Lutze |
| 2009/0117004 | A1 | 5/2009 | Fritchie et al. |
| 2014/0065622 | A1 | 3/2014 | Beebe et al. |
| 2014/0190894 | A1 | 7/2014 | Beebe et al. |

FOREIGN PATENT DOCUMENTS

| | | |
|---|---|---|
| WO | WO2012/052033 | 4/2012 |
| WO | WO2016115028 | 7/2016 |

OTHER PUBLICATIONS

International Search Report and Written Opinion dated Apr. 1, 2016, for International Patent Appl. No. PCT/US2016/012827, 12 pp.

International Search Report and Written Opinion mailed in PCT Application No. PCT/US2017/012082, dated Mar. 17, 2017.

Casavant et al., Efficient Sample Preparation from Complex Biological Samples Using a Sliding Lid for Immobilized Droplet Extractions, Analytical Chemistry, vol. 86, No. 13, May 20, 2014, pp. 6355-6362.

Guckenberger et al., Magnetic System for Automated Manipulation of Paramagnetic Particles, Analytical Chemistry, vol. 88, No. 20, Sep. 6, 2016, pp. 9902-9907.

* cited by examiner

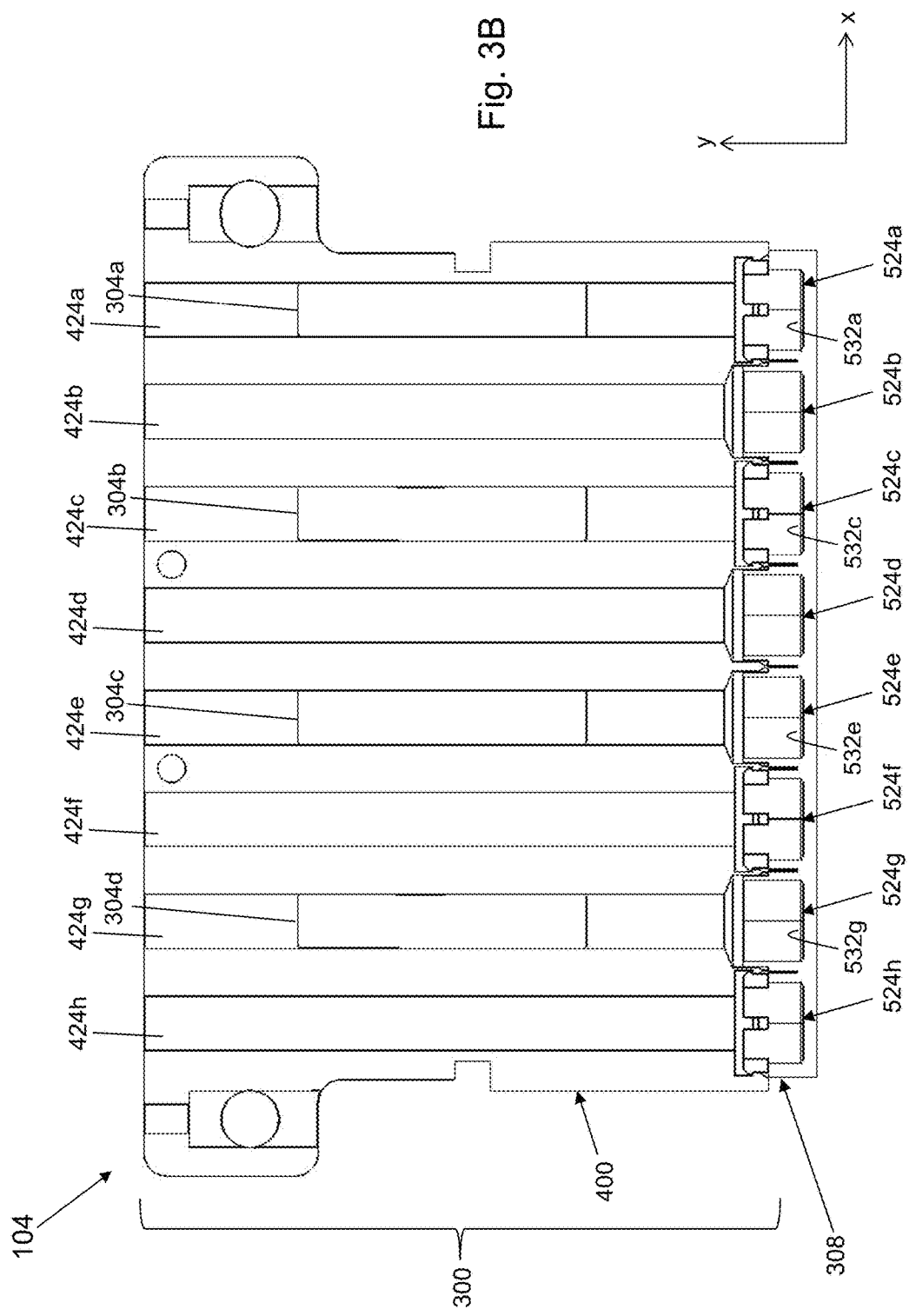

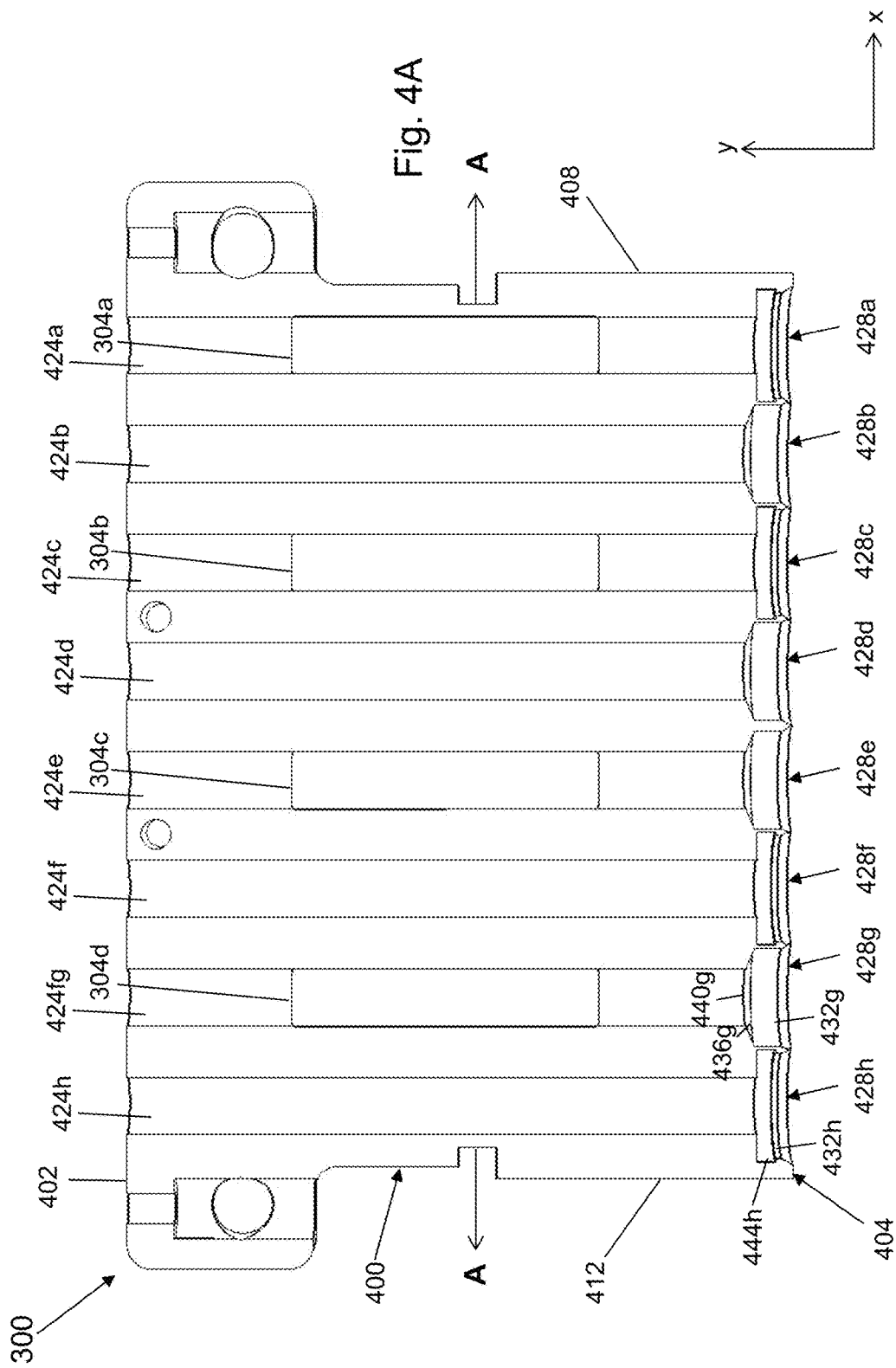

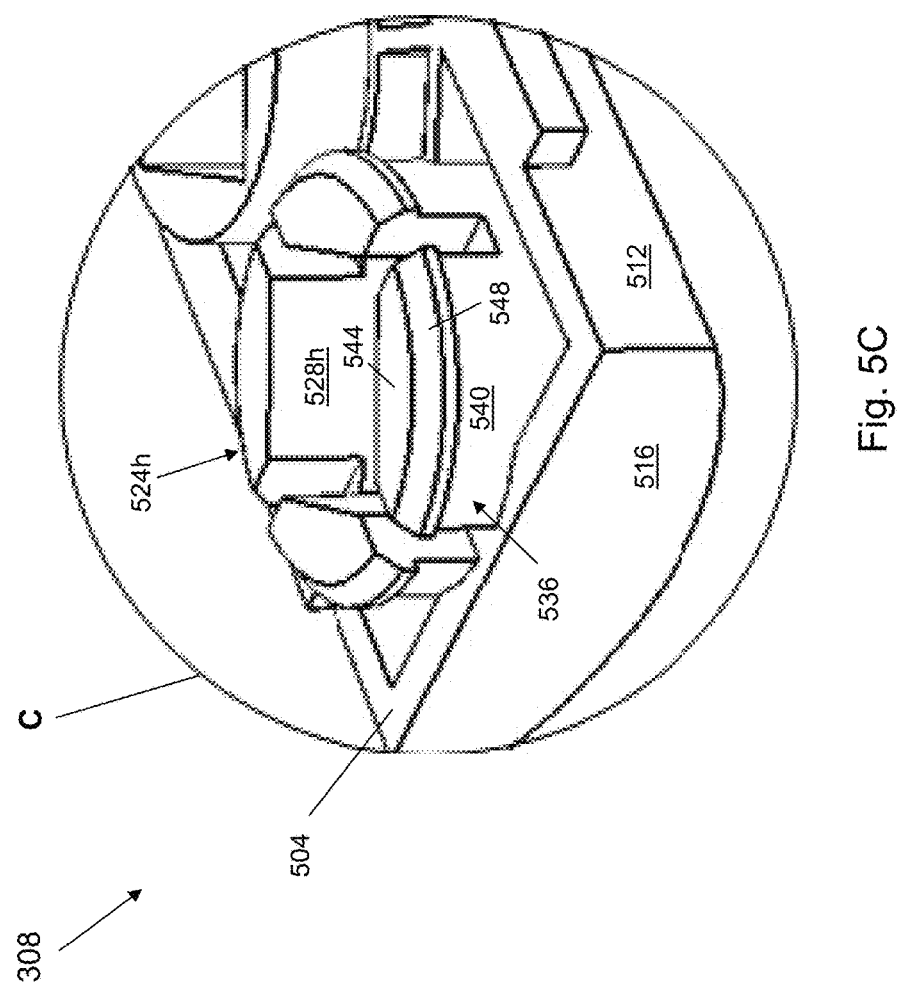

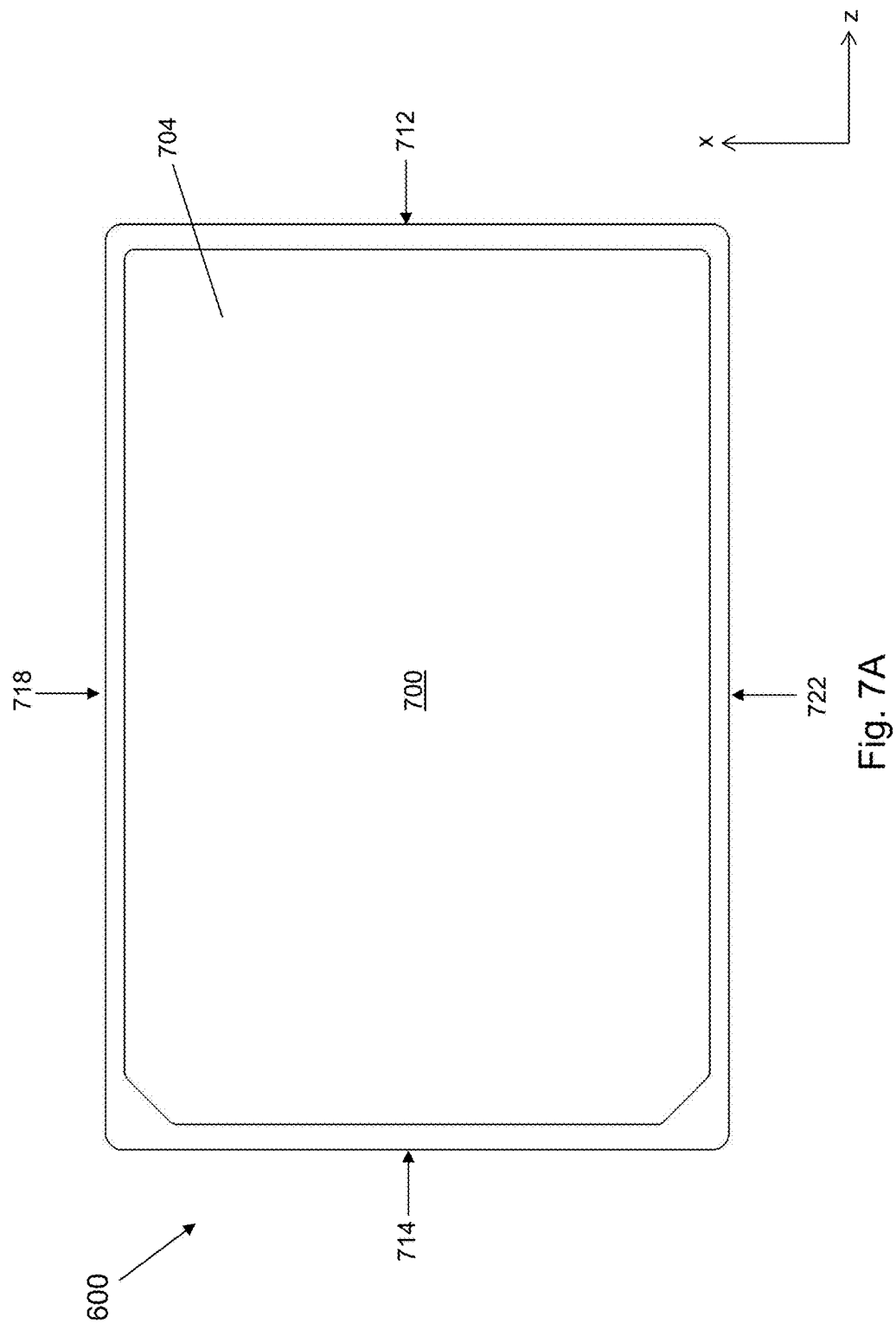

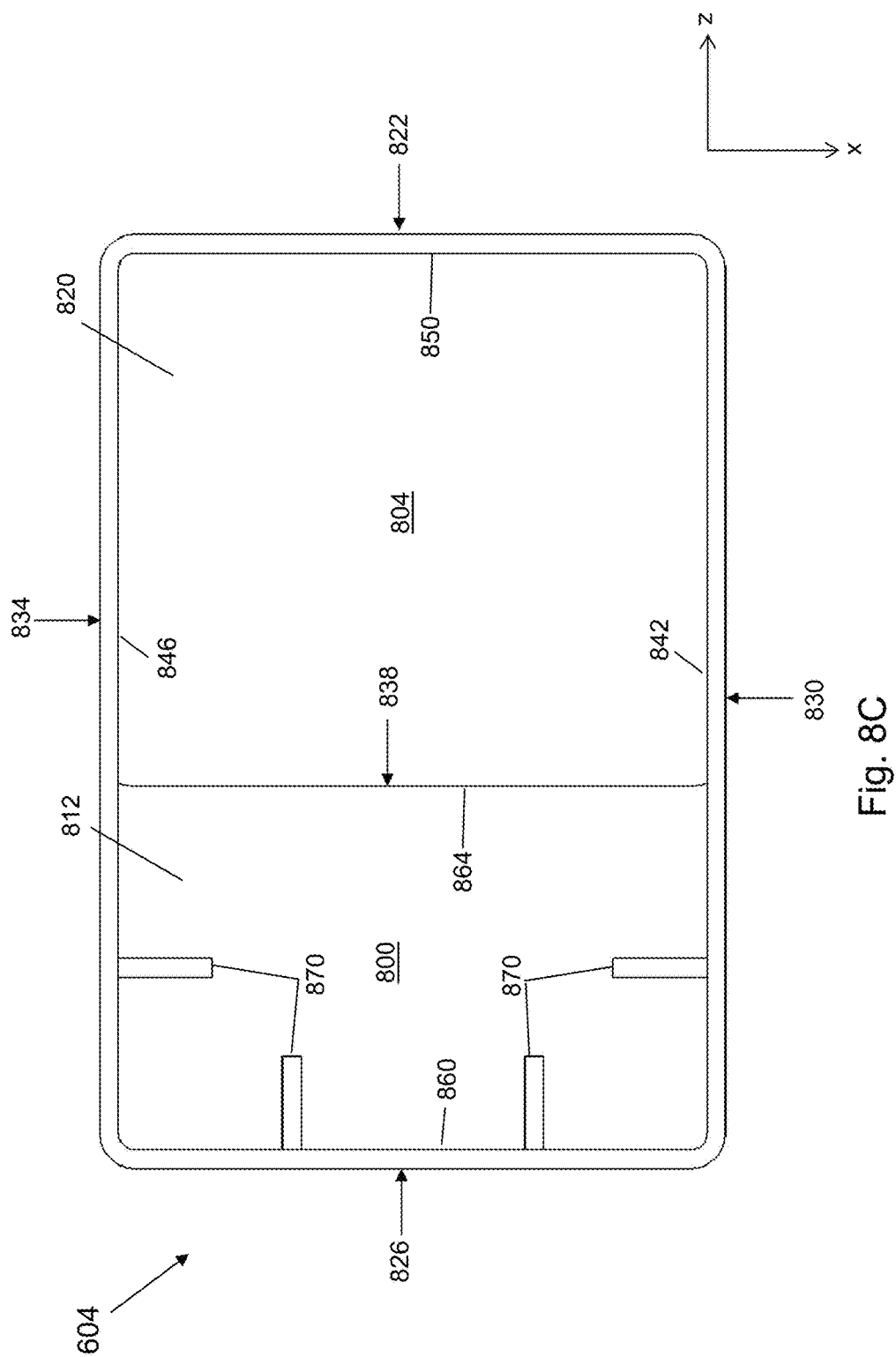

MAGNETIC BASE FOR COLLECTION AND RELEASE OF PARAMAGNETIC PARTICLES

BACKGROUND

Processing of liquid samples to isolate desired components from other components that may be present in the liquid samples is ubiquitous in a variety of fields. For example, DNA sequencing can involve first lysing cells containing the target DNA to form a lysate, a complex mixture of the desired nucleic acids and other components such as cellular debris and lysing reagents. Before the desired nucleic acids can be amplified, detected and quantified, they must be isolated from these other components.

SUMMARY

In one aspect, a magnetic base for a sample plate of a sample processing system is provided comprising a first plate comprising a first top surface; a bottom surface; and a sample plate mounting cavity wall mounted to the first top surface, wherein the first plate and the sample plate mounting cavity wall define a sample plate mounting cavity configured to accommodate a sample plate of a sample processing system. The magnetic base further comprises a second plate extending parallel to the first plate, the second plate comprising a second top surface; and a magnet mounting cavity wall extending between the bottom surface of the first plate and the second top surface of the second plate, wherein the first plate, the second plate, and the magnet mounting cavity wall define a magnet mounting cavity configured to accommodate a free floating magnet.

In another aspect, a sample processing system is provided comprising a base comprising an upper surface and a magnetic base mounted to the upper surface. The magnetic base comprises a first plate comprising a first top surface; a bottom surface; and a sample plate mounting cavity wall mounted to the first top surface, wherein the first plate and the sample plate mounting cavity wall define a sample plate mounting cavity configured to accommodate a sample plate of the sample processing system. The magnetic base further comprises a second plate extending parallel to the first plate, the second plate comprising a second top surface; and a magnet mounting cavity wall extending between the bottom surface of the first plate and the second top surface of the second plate, wherein the first plate, the second plate, and the magnet mounting cavity wall define a magnet mounting cavity configured to accommodate a free floating magnet. The magnetic base further comprises the free floating magnet mounted within the magnet mounting cavity. The sample processing system further comprises the sample plate mounted in the sample plate mounting cavity, the sample plate comprising a plurality of wells. The sample processing system further comprises a magnetic head mounted to the base to translate over the sample plate in a translation direction, the magnetic head comprising a housing comprising a channel, a top magnet mounted in the channel such that the top magnet is movable within the channel between an upper position and a lower position relative to the first top surface of the first plate.

Other principal features and advantages of the disclosure will become apparent to those skilled in the art upon review of the following drawings, the detailed description, and the appended claims.

BRIEF DESCRIPTION OF THE DRAWINGS

Illustrative embodiments of the disclosure will hereafter be described with reference to the accompanying drawings, wherein like numerals denote like elements.

FIG. 3B depicts a front, cross-sectional view of the magnetic head of FIG. 3A.

FIG. 4A depicts a front, cross-sectional view of a housing of the magnetic head of FIG. 3A.

FIG. 5C depicts an enlarged view of a portion of the adapter of FIG. 5A.

FIG. 7A depicts a top view of a cover portion of the magnetic base of FIG. 6A.

FIG. 8C depicts a bottom view of the base portion of FIG. 8A.

DETAILED DESCRIPTION

Figure 1:
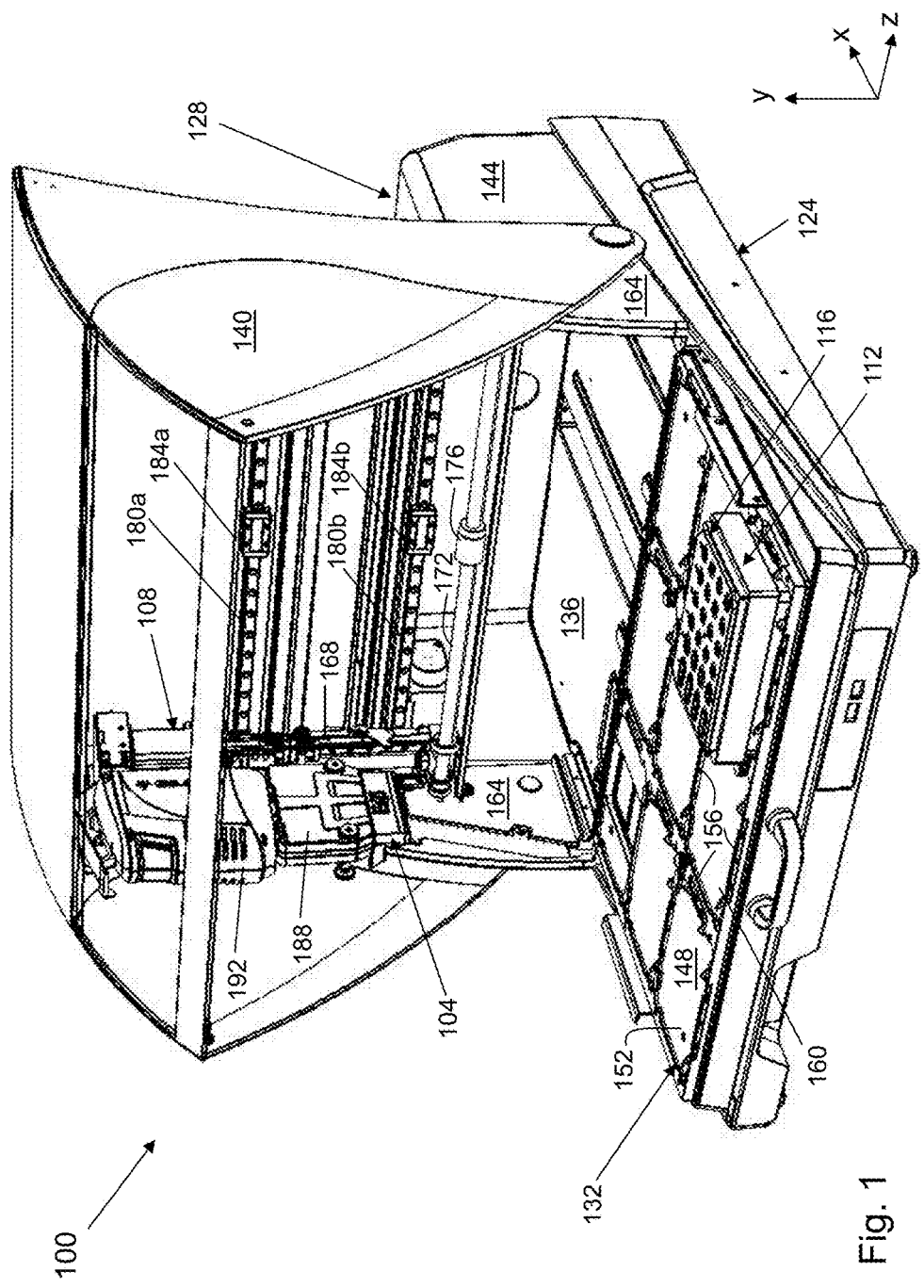
FIG. 1 depicts a perspective view of a sample processing system in accordance with an illustrative embodiment.

With reference to FIG. 1, a perspective view of a sample processing system 100 for processing liquid samples shown in accordance with an illustrative embodiment. Sample processing system 100 may include a magnetic head 104, a drive system 108, a magnetic base 112, and a sample plate 116. Sample processing system 100 may also include a support assembly configured to support and enclose various components of sample processing system 100. By way of illustration, the support assembly may include a base 124, a cover 128, and a work bed 132. Sample processing system 100 may include additional, fewer, or different components. As shown in the illustrative embodiment, sample processing system 100 may be an automated system in which at least some of the components of sample processing system 100 are moved under electronic controls automatically.

Sample processing system 100 may be used to isolate target analytes from a liquid sample in a well of sample plate 116 in which target analytes have been bound to a solid substrate (e.g., paramagnetic beads). Sample processing system 100 may isolate target analytes by moving solid substrate bound with target analytes from liquid sample to one or more other liquid-filled wells of sample plate 116 via a plurality of top magnets 304a-d (with reference to FIG. 3B) mounted in magnetic head 104 in conjunction with a bottom magnet 608 (with reference to FIG. 8A) mounted in magnetic base 112. Operation of sample processing system 100 involves collecting solid substrate bound with target analytes from the liquid sample of the well of sample plate 116, moving solid substrate bound with target analytes to one of the other liquid-filled wells, and releasing solid substrate bound with target analytes into the liquid-filled well.

As used herein, the term "mount" includes join, unite, connect, couple, associate, insert, hang, hold, affix, attach, fasten, bind, paste, secure, bolt, screw, rivet, solder, weld, glue, form over, form in, layer, mold, rest on, rest against, abut, and other like terms. The phrases "mounted on", "mounted to", and equivalent phrases indicate any interior or exterior portion of the element referenced. These phrases also encompass direct mounting (in which the referenced elements are in direct contact) and indirect mounting (in which the referenced elements are not in direct contact, but are connected through an intermediate element). Elements referenced as mounted to each other herein may further be integrally formed together, for example, using a molding or thermoforming process as understood by a person of skill in the art. As a result, elements described herein as being mounted to each other need not be discrete structural elements. The elements may be mounted permanently, removably, or releasably unless specified otherwise.

In addition, use of directional terms, such as top, bottom, right, left, front, back, upper, lower, etc. are merely intended to facilitate reference to various surfaces that form components of the devices referenced herein and are not intended to be limiting in any manner.

Sample processing system 100 may be used to process any type of liquid sample (e.g., biological sample) in order to isolate a variety of types of target analytes (e.g., proteins, nucleic acids, cells, etc.) from other components which may be present in liquid sample (e.g., solvent, blood, urine, sputum, plants, cells, etc.). As such, sample processing system 100 may be used as a platform for DNA or protein purification, cell separation, etc. Such techniques are widely used in basic laboratory research, drug discovery, disease diagnosis and monitoring, etc.

Figure 2A:
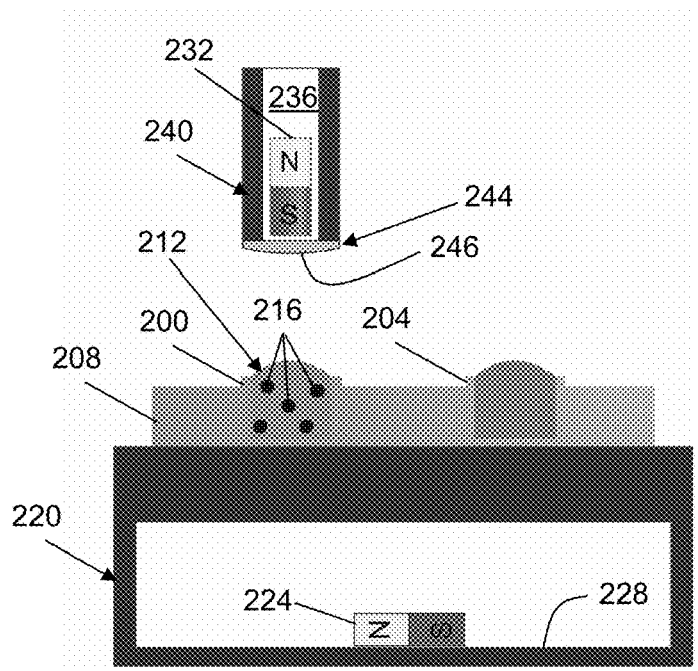
FIGS. 2A-2E depict a method of isolation performed by the sample processing system of FIG. 1A.

Illustrative operations performed by sample processing system 100 are schematically shown in FIGS. 2A-2E. As shown in FIG. 2A, a first well 200 and a second well 204 are mounted to a surface of a sample plate 208. (Sample plate 116 of FIG. 1 is an illustrative embodiment of sample plate 208.) A liquid sample 212 is deposited in first well 200. Liquid sample 212 may include a variety of components, including target analytes (e.g., cells) bound to a plurality of particles 216. Particles 216 may be magnetic, paramagnetic, or ferromagnetic.

Sample plate 208 is mounted to a surface of a magnetic base 220. (Magnetic base 112 of FIG. 1 is an illustrative embodiment of magnetic base 220.) Magnetic base 220 defines a cavity in which a bottom magnet 224 is mounted. Bottom magnet 224 is free floating within magnetic base 220. By "free floating" it is meant that bottom magnet 224 is mounted within magnetic base 220 such that it is able to move substantially freely relative to inner surfaces of magnetic base 220. In FIG. 2A, bottom magnet 224 rests on a bottom inner surface 228 of magnetic base 220. The phrase "substantially freely" and the like are meant to recognize that the movement of a target component (e.g., bottom magnet 224) may not be perfectly free but that the movement is not restricted to any significant degree.

Positioned over first well 200 is a top magnet 232 mounted within a channel 236 of a magnetic head 240. (Magnetic head 104 of FIG. 1 is an illustrative embodiment of magnetic head 240.) An adapter 244 having a bottom surface 246 is also mounted to magnetic head 240. Adapter 244 forms an interface between top magnet 232 and liquid in first and second wells 200, 204 and provides bottom surface 246 onto which particles 216 are collected as well as from which particles 216 are released. Top magnet 232 may be moved between an upper position and a lower position within channel 236 relative to adapter 244. In FIG. 2A, top magnet 232 is shown in its lower position.

Figure 2B:
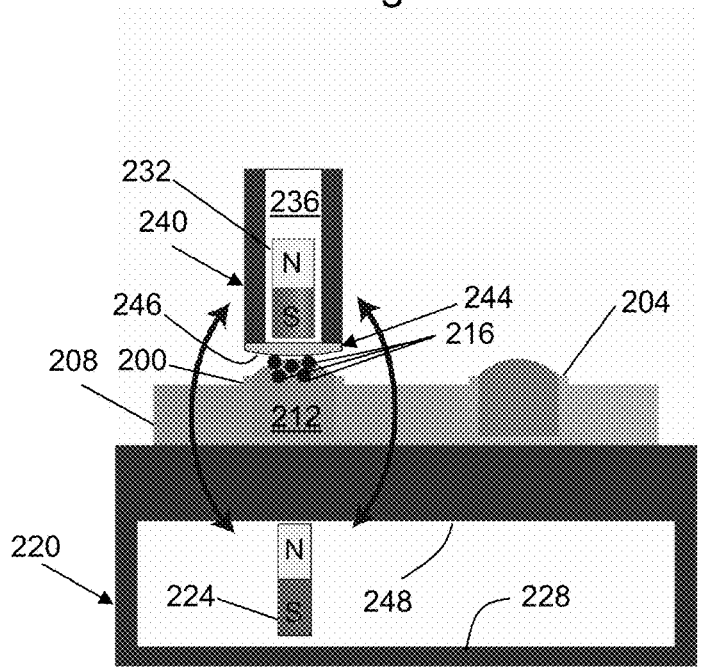

In a first step as depicted in FIG. 2B, with top magnet 232 in its lower position within channel 236, magnetic head 240 is lowered over first well 200 such that a magnetic force from top magnet 232 attracts and holds particles 216 bound with target analytes to bottom surface 246 of adapter 244. The magnetic force from top magnet 232 also attracts and holds bottom magnet 224 to a top inner surface 248 of magnetic base 220. Because top magnet 232 is in closer proximity to particles 216 than bottom magnet 224 is to particles 216, particles 216 are collected onto bottom surface 246 of adapter 244.

Figure 2C:
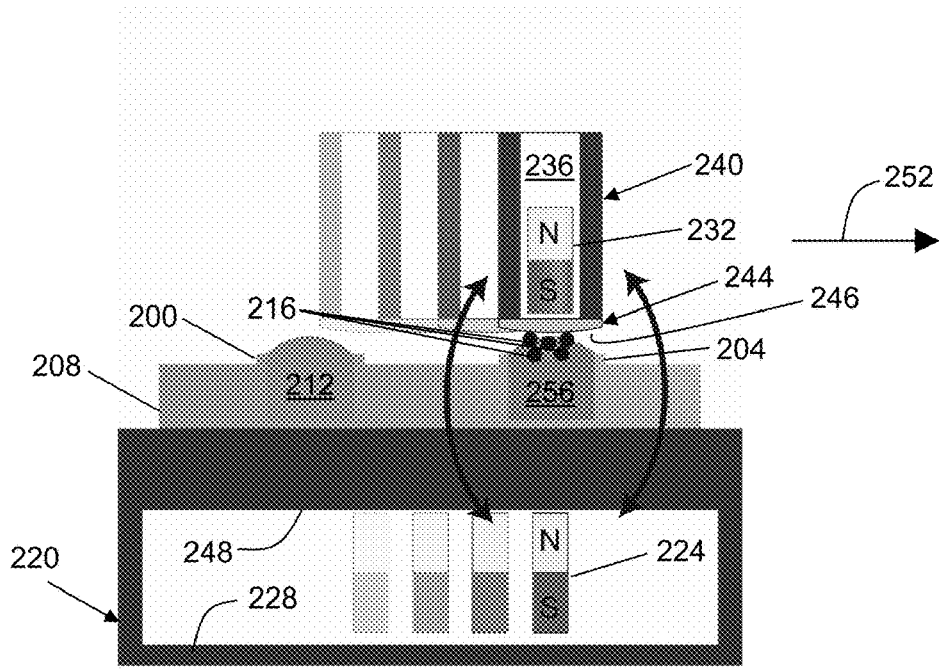

In a second step as depicted in FIG. 2C, magnetic head 240 is translated along in a direction shown by an axis 252 until magnetic head 240 with top magnet 232 is positioned over second well 204. Due to the magnetic force from top magnet 232, bottom magnet 224 tracks top magnet 232 and is simultaneously translated along top inner surface 248 of magnetic base 220 in the direction shown by axis 252 to a position below second well 204. A liquid 256 may be deposited in second well 204. Liquid 256 may include a processing reagent (e.g., stain) for modifying target analytes. Particles 216 bound with target analytes are immersed in liquid 256 of second well 204 when top magnet 232 is positioned over second well 204. Other components of liquid sample 212 that were not bound to particles 216 may remain within first well 200.

Figure 2D:
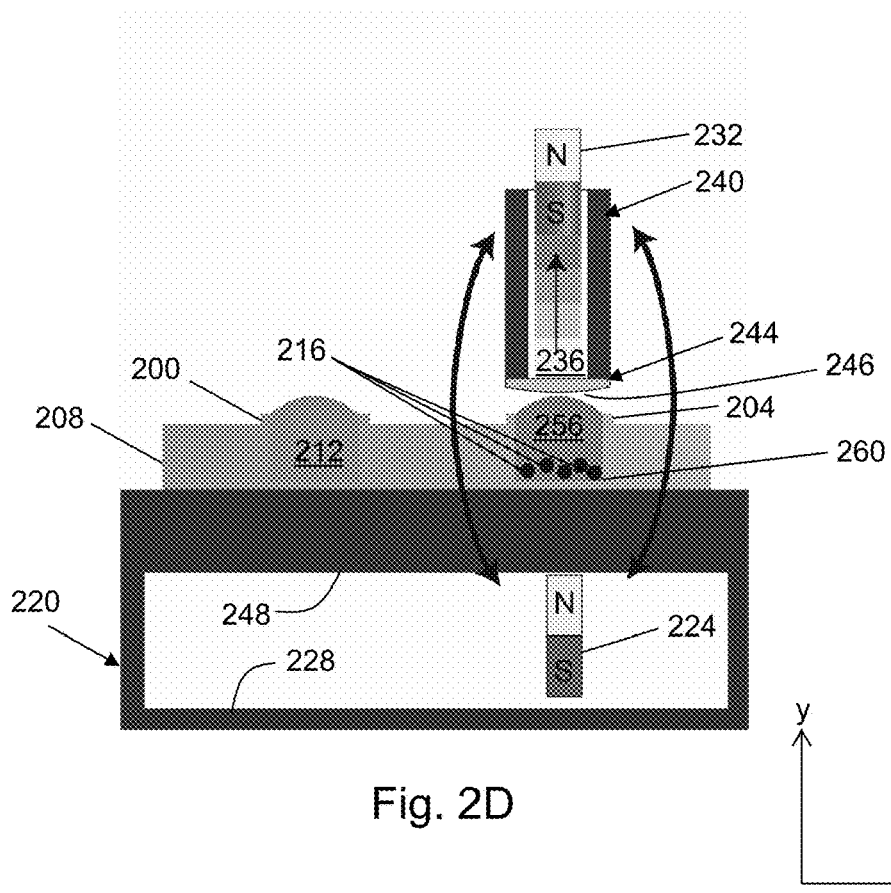

In a third step as depicted in FIG. 2D, top magnet 232 is moved to its upper position within channel 236 such that the magnetic force from top magnet 232 still attracts and holds bottom magnet 224 to top inner surface 248 of magnetic base 220. However, bottom magnet 224 is now in closer proximity to particles 216 than top magnet 232 is to particles 216. Thus, particles 216 are attracted to a bottom surface 260 of second well 204, thereby releasing particles 216 from bottom surface 246 of adapter 244.

Figure 2E:
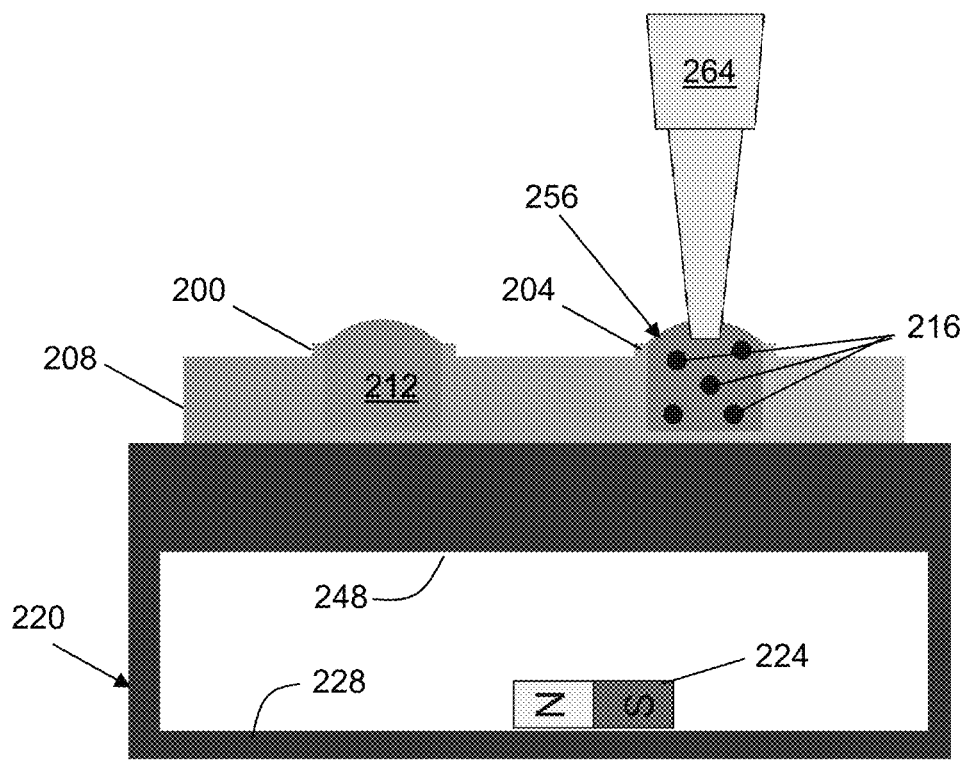

In a fourth step as depicted in FIG. 2E, magnetic head 240 is moved or translated away from sample plate 208 such that bottom magnet 224 is released from top inner surface 248 and falls back onto bottom inner surface 228 of magnetic base 220. Both top magnet 232 and bottom magnet 224 exert negligible magnetic force on particles 216. In the absence of any substantial magnetic force, particles 216 subsequently disperse within liquid 256 of second well 204. Liquid 256, including particles 216 with the now processed and isolated target analytes (e.g., stained cells), may be freely mixed and resuspended (e.g., via a pipette 264). Particles 216 bound with target analytes may then be removed for further analysis or be recollected and moved to additional wells mounted to sample plate 208 as described in FIGS. 2A-2D. The phrase "absence of any substantial magnetic force" and the like is meant to recognize that the magnetic force may not be perfectly zero but is sufficiently small such that it cannot alter the movement of a target component (e.g., particles 216) to any significant degree.

FIGS. 2B and 2C represent "collect" operational states of sample processing system 100; FIG. 2D represents a "release" operational state of sample processing system 100; and FIG. 2E represents a "disperse" operational state of sample processing system 100.

With reference back to FIG. 1, base 124, cover 128 and work bed 132 may form part of the support assembly configured to support and enclose various components of sample processing system 100. Base 124 may include a base plate 136 and a plurality of walls extending down from base plate 136. Cover 128 may include a first cover portion 140 and a second cover portion 144. Each of first cover portion 140 and second cover portion 144 may also include a plurality of walls configured to enclose various components of sample processing system 100.

Work bed 132 may include a support plate 148 having a top surface 152. Support plate 148 may be mounted to a translating plate (not shown) positioned underneath support plate 148. Support plate 148 may include a plurality of ridges (three ridges 156 of which are labeled in FIG. 1) extending up from top surface 152. The plurality of ridges defines a plurality of cavities, one cavity 160 of which is labeled in FIG. 1. The plurality of cavities may be configured to receive magnetic base 112 on which sample plate 116 is mounted. For illustration, magnetic base 112 is shown mounted to a cavity positioned immediately to the right of cavity 160. Other components may also be mounted on support plate 148 via the plurality of cavities, e.g., a rack configured to hold one or more receptacles (e.g., vials, test tubes, etc.) that are configured to hold samples or liquids to be transferred to (or from) sample plate 116.

Drive system 108 of sample processing system 100 is configured to control movement of magnetic head 104. Drive system 108 may include side walls 164, a device support structure 168, a lead screw 172, a lead screw interface 176, a top bearing rail 180a, a bottom bearing rail 180b, a top bearing rail interface 184a, and a bottom bearing rail interface 184b. Side walls 164 may be mounted to base 124 and extend up from base plate 136. Lead screw 172 may be mounted to side walls 164. Lead screw 172 may also be mounted to lead screw interface 176. Lead screw interface 176 may be mounted to device support structure 168 so that device support structure 168 may translate along lead screw 172. Bearing rails 180a, 180b may be mounted to side walls 164. Bearing rails 180a, 180b may also be mounted to bearing rail interfaces 184a, 184b, respectively. Bearing rail interfaces 184a, 184b may further be mounted to device support structure 168 so that device support structure 168 may also translate along bearing rails 180a, 180b. Magnetic head 104 may be mounted to device support structure 168 such that the plurality of top magnets 304a-d mounted in magnetic head 104 are aligned approximately perpendicular relative to sample plate 116.

Drive system 108 may further include one or more actuators (not shown) to control movement of device support structure 168 along lead screw 172 so as to position magnetic head 104 over sample plate 116. Various types of actuators may be used, e.g., an electric motor, a servo, stepper, or piezo motor, a pneumatic actuator, a gas motor, etc. Drive system 108 may provide movement of device support structure 168 (and thus, magnetic head 104) in one-dimension, two-dimensions, or three-dimensions relative to support plate 148 and to sample plate 116 mounted thereon. By way of illustration, drive system 108 may provide movement of magnetic head 104 in two-dimensions (y-z) relative to support plate 148. During operation of sample processing system 100, the axis of translation of magnetic head 104 relative to sample plate 116 is along the z-axis.

Sample processing system 100 may include a plurality of drive systems, including drive system 108 and a second drive system (not shown). The second drive system may be configured to control movement of support plate 148 in one-dimension (x) relative to base 124 in conjunction with the translating plate (not shown) mounted underneath support plate 148.

Magnetic head 104 and support plate 148 may be moved under electronic controls automatically via a controller (not shown) operably coupled to drive system 108 and the second drive system. One or more components of the controller may be mounted on a printed circuit board (not shown) mounted to a component of sample processing system 100 (e.g., a bottom surface of base plate 136).

Figure 3A:
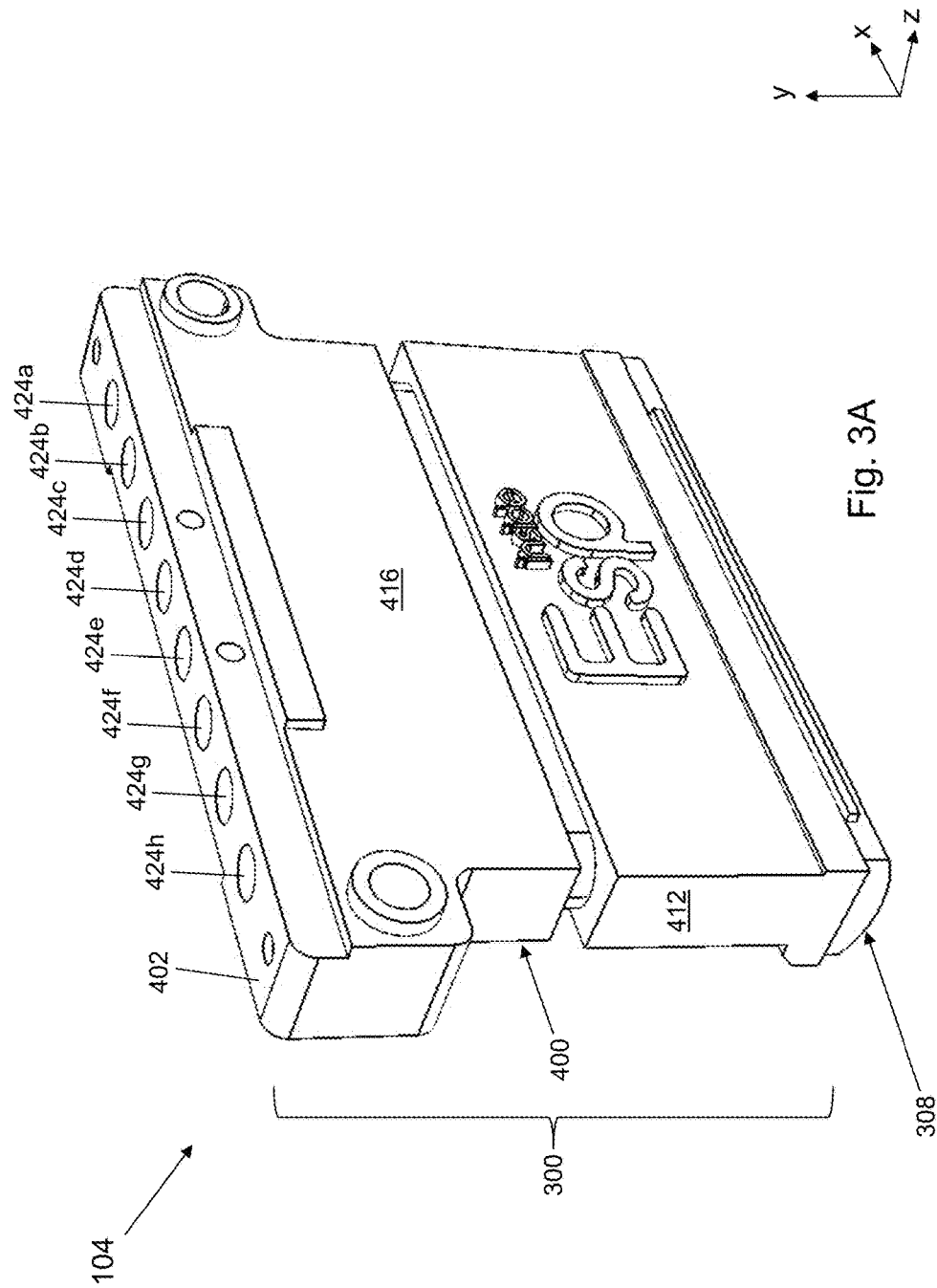
FIG. 3A depicts a perspective view of a magnetic head of the sample processing system of FIG. 1.

With reference to FIGS. 3A-3B, views of magnetic head 104 of sample processing system 100 are shown according to an illustrative embodiment. FIG. 3A shows a perspective view of magnetic head 104. FIG. 3B shows a front, cross-sectional view of magnetic head 104.

Magnetic head 104 is configured to accommodate the plurality of top magnets 304a-d, each top magnet of which provides a magnetic force for collecting a plurality of magnetic particles (e.g., paramagnetic beads) from liquid contained in wells of sample plate 116 of sample processing system 100. The magnetic force also attracts and holds bottom magnet 608 of magnetic base 112 during such collection. Magnetic head 104 may include a housing 300, the plurality of top magnets 304a-d, and an adapter 308. Magnetic head 104 may include fewer, additional or different components. Magnetic head 104 is an illustrative embodiment of magnetic head 240 of FIGS. 2A-2E and adapter 308 is an illustrative embodiment of adapter 244 of FIGS. 2A-2E.

Figure 4B:
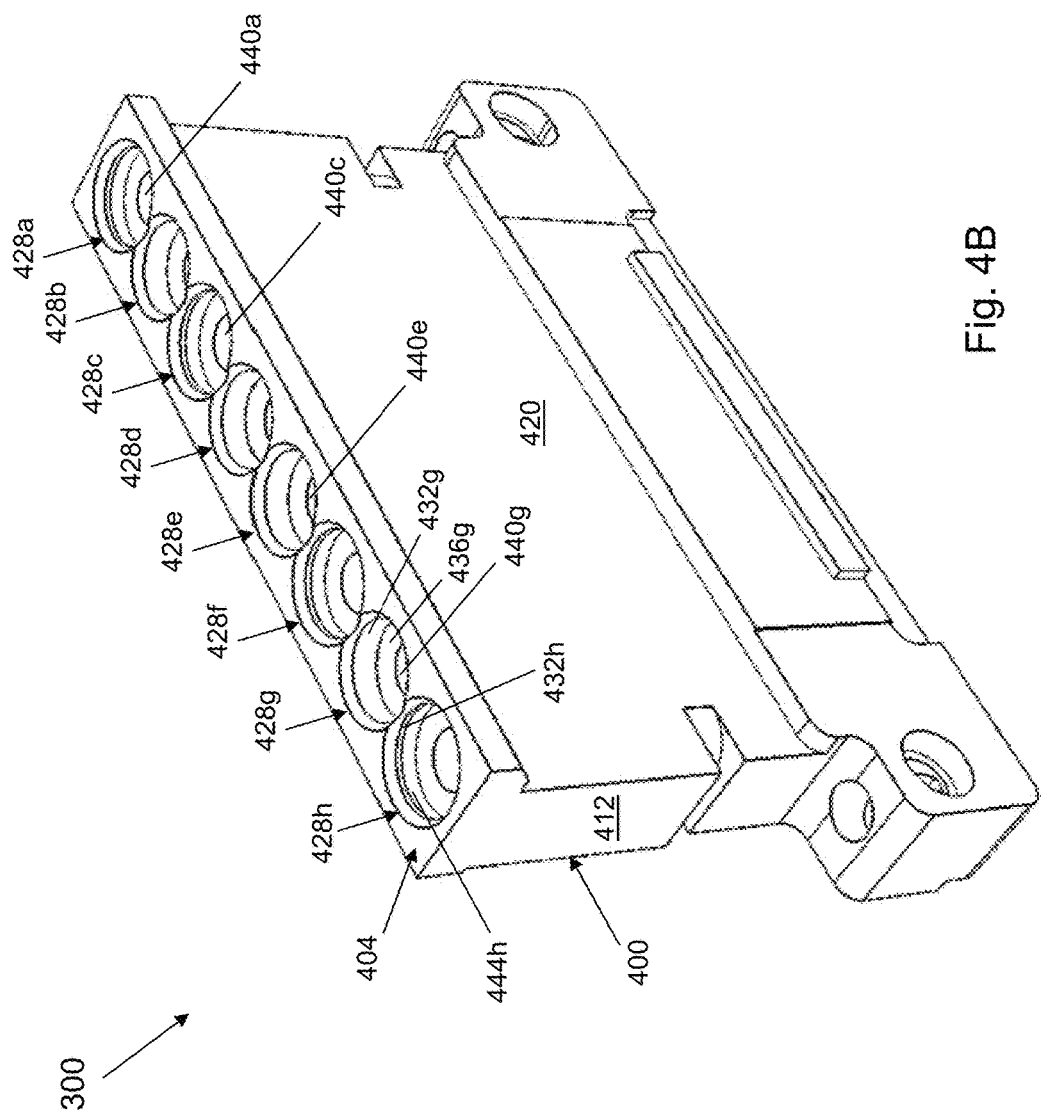
FIG. 4B depicts a bottom, perspective view of the housing of FIG. 4A.

With reference to FIGS. 4A-4B, views of housing 300 of magnetic head 104 are shown. FIG. 4A shows a front, cross-sectional view of housing 300. FIG. 4B shows a bottom, perspective view of housing 300 (housing 300 has been rotated 180° about axis A of FIG. 4A). Housing 300 may include a plate 400 having a top surface 402, a bottom surface 404, a right side surface 408, a left side surface 412, a front surface 416 (with respect to FIG. 3A) and a back surface 420. Housing 300 may include a plurality of channels 424a-h extending from top surface 402 to bottom surface 404 and parallel to right and left side surfaces 408, 412 and parallel to front and back surfaces 416, 420. The plurality of channels 424a-h may be arranged as a linear array. Channels 424a, 424c, 424e, 424g of the plurality of channels 424a-h receive a top magnet of the plurality of top magnets 304a-d, respectively, such that top magnet 304a is mounted in channel 424a; top magnet 304b is mounted in channel 424c; top magnet 304c is mounted in channel 424e;

and top magnet 304*d* is mounted in channel 424*g*. Channels 424*b*, 424*d*, 424*f*, 424*h* may be similarly configured to channels 424*a*, 424*c*, 424*e*, 424*g*, although in the illustrative embodiment, channels 424*b*, 424*d*, 424*f*, 424*h* are blank channels which do not receive a top magnet. Various numbers of channels and various numbers of top magnets may be used.

Channels 424*a*, 424*c*, 424*e*, 424*g* of the plurality of channels 424*a-h* may also receive a piston of a plurality of pistons (not shown), each piston mounted above a respective top magnet. The plurality of pistons may form part of a third drive system (not shown) of the plurality of drive systems of sample processing system 100.

The third drive system is configured to control the movement of each top magnet of the plurality of top magnets 304*a-d* within its respective channel (424*a*, 424*c*, 424*e*, 424*g*) so as to position each top magnet in an upper position and a lower position relative to bottom surface 404 of housing 300. In FIGS. 3B and 4A, each top magnet of the plurality of top magnets 304*a-d* is shown positioned in its upper position. Thus, the third drive system may provide movement of each top magnet of the plurality of top magnets 304*a-d* in one-dimension (y) relative to support plate 148 and sample plate 116 mounted thereon (see FIG. 1). The third drive system may provide such movement independently from the movement of magnetic head 104 provided by drive system 108. In this way, drive system 108 may be used to position magnetic head 104 over sample plate 116 such that each top magnet of the plurality of top magnets 304*a-d* is centered over a respective well of a column of wells (see, e.g., column 5 of sample plate 116 in FIG. 11A) and such that adapter 308 is in contact with the liquid in each respective well. The third drive system may be used to move each top magnet of the plurality of top magnets 304*a-d* within its respective channel (424*a*, 424*c*, 424*e*, 424*g*) between its upper position and its lower position relative to the liquid in each respective well.

One or more components of the third drive system may be enclosed by a first cover 188 and a second cover 192 (see FIG. 1), first and second covers 188, 192 mounted to magnetic head 104. The third drive system may achieve movement of the plurality of top magnets 304*a-d* via a variety of known actuators and is not limited to use of the plurality of pistons. The plurality of top magnets 304*a-d* may be moved under electronic controls automatically via a second controller (not shown) operably coupled to the third drive system. One or more components of the second controller may be mounted on a second printed circuit board (not shown) enclosed by second cover 192.

Each top magnet of the plurality of top magnets 304*a-d* is composed of a magnetic material (e.g., a permanent magnetic material). The magnetic material and the size and shape of each top magnet may be selected to produce a magnetic force sufficient to attract the plurality of magnetic particles in the liquid of the wells of sample plate 116 when each top magnet of the plurality of top magnets 304*a-d* is centered over a respective well of sample plate 116, adapter 308 is in contact with the liquid in each respective well, and each top magnet is in its lower position. At the same time, the magnetic force may also be that which is sufficient to attract and hold bottom magnet 608 of magnetic base 112. Each top magnet of the plurality of top magnets 304*a-d* may be configured as a bar with a square-shaped cross-section or a rod, the greatest dimension of which may be referred to as a length of the bar or rod. Each top magnet of the plurality of top magnets 304*a-d* may be polarized across its length, by which it is meant that its axis of magnetization is across its length (see FIGS. 2A-2E, showing top magnet 232 having an axis of magnetization across its length, parallel to channel 236).

Bottom surface 404 of housing 300 may include a plurality of recesses 428*a-h* formed therein. Each recess of the plurality of recesses 428*a-h* has side walls that extend from bottom surface 404 towards top surface 402 of housing 300 and an inner surface. A side wall 432*g* and an inner surface 436*g* of recess 428*g* are labeled for illustration. Recesses 428*a*, 428*c*, 428*e* and 428*g* may each include an aperture 440*a*, 440*c*, 440*e*, 440*g*, respectively, formed in each respective inner surface which is shaped and sized to allow an end of a top magnet of the plurality of top magnets 304*a-d* to pass through and to extend into a respective recess, e.g., when each top magnet is moved from its upper position to its lower position. When each top magnet of the plurality of magnets 304*a-d* is moved into its lower position, an end of top magnet 304*a* extends through aperture 440*a* into recess 428*a*; an end of top magnet 304*b* extends through aperture 440*c* into recess 428*c*; an end of top magnet 304*c* extends through aperture 440*e* into recess 428*e*; and an end of top magnet 304*d* extends through aperture 440*g* into recess 428*g*. Recesses 428*b*, 428*d*, 428*f*, and 428*h* may be configured similarly to recesses 428*a*, 428*c*, 428*e* and 428*g*, although in the illustrative embodiment, recesses 428*b*, 428*d*, 428*f*, and 428*h* do not receive a top magnet.

Adapter 308 may be mounted to bottom surface 404 of housing 300. Thus, one or more of the plurality of recesses 428*a-h* of bottom surface 404 may include a groove formed in side walls configured to receive tabs (e.g., a tab 548 with reference to FIG. 5C) on projections (e.g., a projection 536 with reference to FIG. 5C) of adapter 308 to mount adapter 308 to bottom surface 404. A groove 444*h* formed in side wall 432*h* of recess 428*h* is labeled for illustration. Recesses 428*a*, 428*c* and 428*f* may be similarly configured.

Housing 300 may be formed from a single piece of material or from multiple pieces of material mounted together. A variety of materials, e.g., plastic, may be used.

Figure 5A:
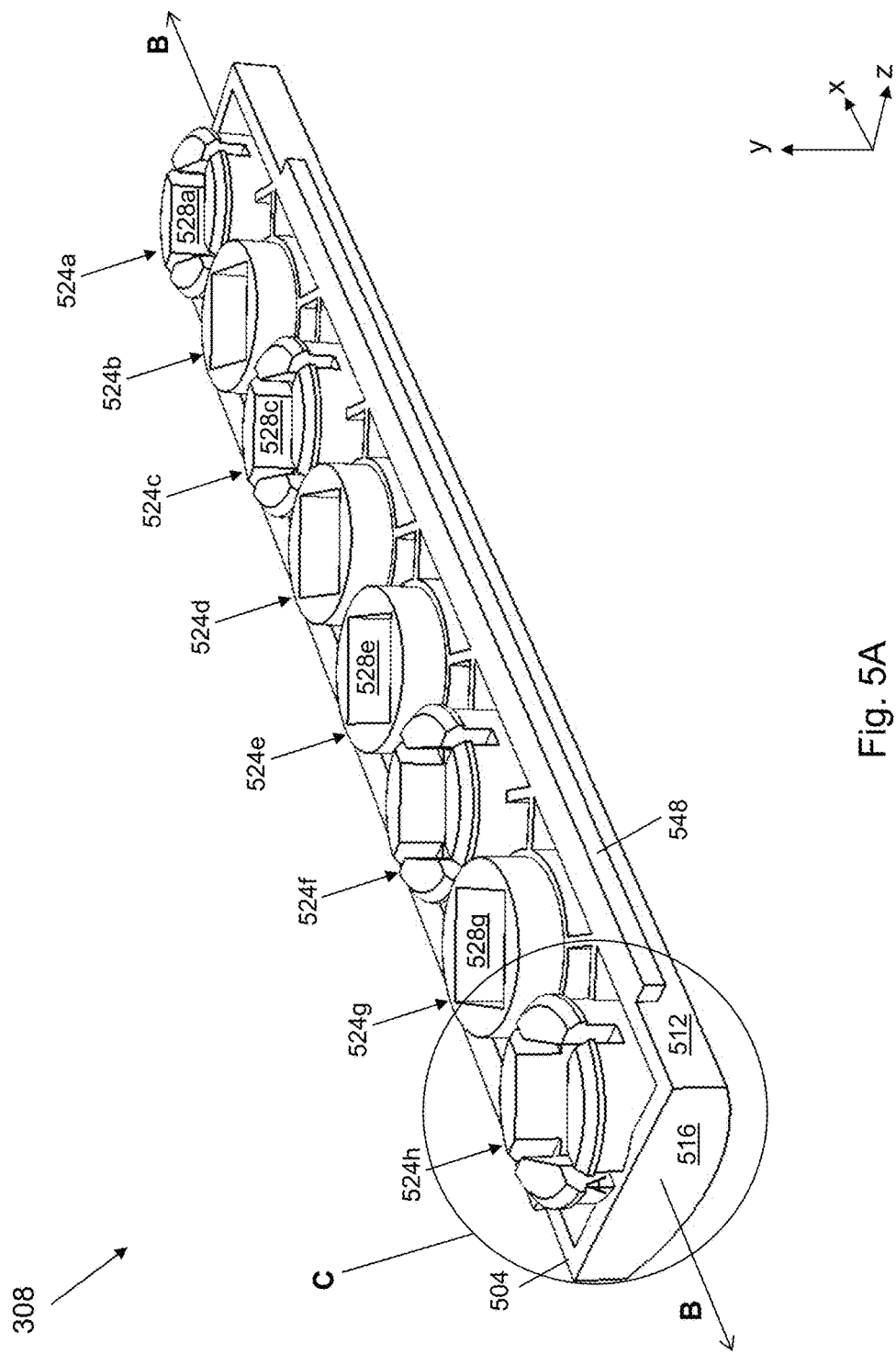
FIG. 5A depicts a top, perspective view of an adapter of the magnetic head of FIG. 3A.
Figure 5B:
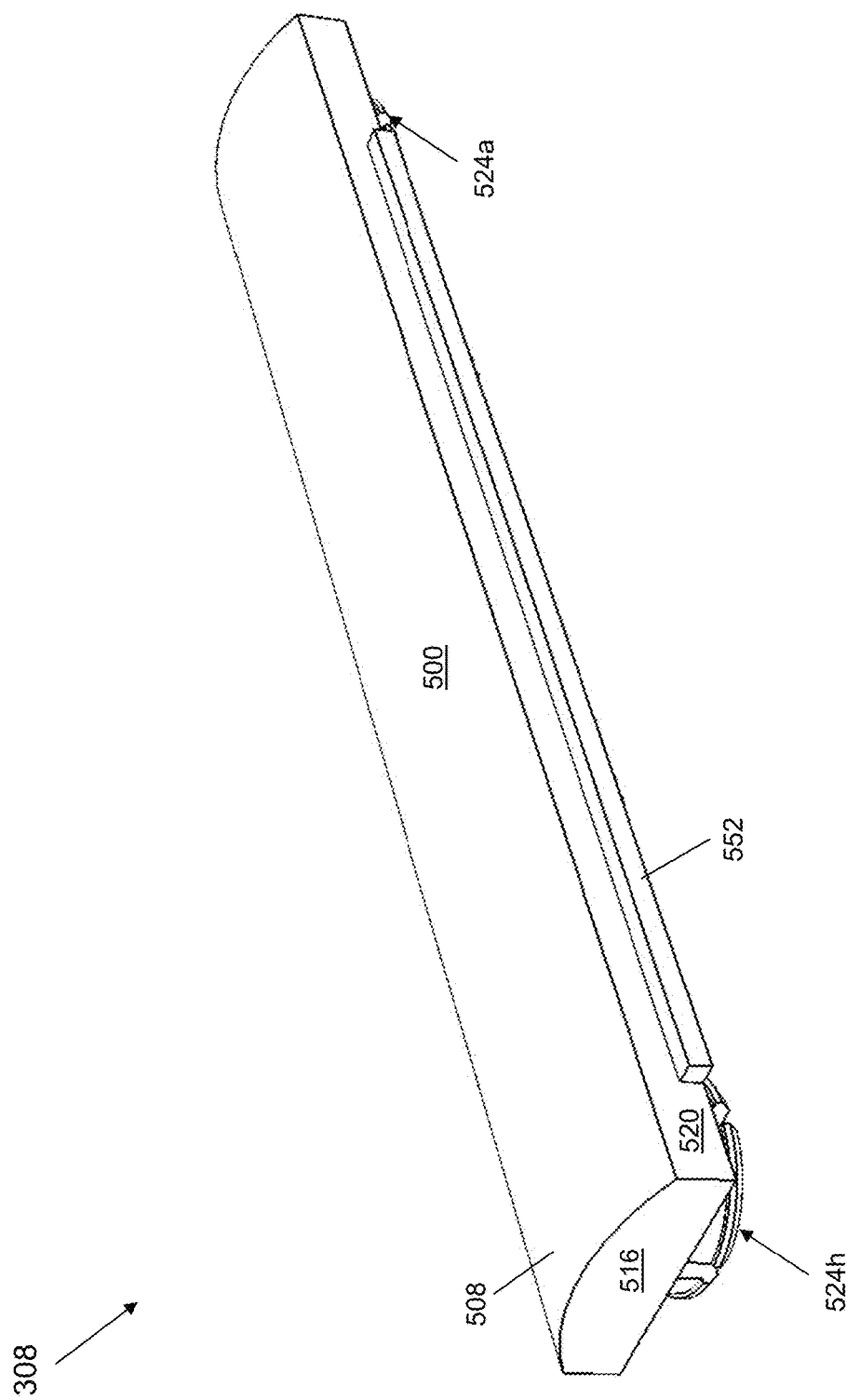
FIG. 5B depicts a bottom, perspective view of the adapter of FIG. 5A.

With reference to FIGS. 5A-5C, views of adapter 308 of magnetic head 104 are shown. FIG. 5A shows a top, perspective view of adapter 308. FIG. 5B shows a bottom, perspective view of adapter (adapter has been rotated 180° about axis B of FIG. 5A). FIG. 5C shows an enlarged view of section C of FIG. 5A.

Adapter 308 is configured to provide an interface between the plurality of top magnets 304*a-d* mounted in housing 300 of magnetic head 104 and liquid in the wells of sample plate 116. Adapter 308 may include an adapter plate 500 that includes a top surface 504, a bottom surface 508, a front wall 512, a left side wall 516, a right side wall (not shown), and a back wall 520. Walls 512, 516, 520 and the right side wall extend between top surface 504 and bottom surface 508 of adapter plate 500. Top surface 504 of adapter plate 500 may form part of a mounting surface of adapter 308 configured to mount to the plurality of top magnets 304*a-d* and to bottom surface 404 of housing 300 of magnetic head 104. Bottom surface 508 of adapter plate 500 may form part of a collection and release surface of adapter 308 configured to collect the plurality of magnetic particles from liquid contained in certain wells of sample plate 116; to hold the plurality of magnetic particles as adapter 308 moves through the liquid as magnetic head 104 translates over sample plate 116; and to release the plurality of magnetic particles into liquid contained in other wells of sample plate 116.

Adapter 308 may be configured to mount to the plurality of top magnets 304*a-d* of magnetic head 104. Thus, adapter plate 500 may include a plurality of recesses 524*a-h* extending from top surface 504 of adapter plate 500 towards bottom surface 508. Each recess of the plurality of recesses 524a-h may correspond to a respective recess of the plurality of recesses 428a-h of bottom surface 404 of housing 300 of magnetic head 104. Each recess of the plurality of recesses 524a-h of adapter 308 has side walls and a bottom surface that define an opening. Side walls 528a, 528c, 528e, and 528g of recesses 524a, 524c, 524e, and 524g are labeled. With reference to FIG. 3B, bottom surfaces 532a, 532c, 532e, and 532g of recesses 524a, 524c, 524e, and 524g of adapter 308 are also labeled.

The opening of recesses 524a, 524c, 524e, and 524g may be sized and shaped to accommodate an end of a top magnet of the plurality of top magnets 304a-d, e.g., when the top magnet is moved from its upper position to its lower position. When adapter 308 is mounted to housing 300 of magnetic head 104 and the plurality of top magnets 304a-d is moved into its lower position, an end of top magnet 304a rests on bottom surface 532a of recess 524a; an end of top magnet 304b rests on bottom surface 532c of recess 524c. An end of top magnet 304c rests on bottom surface 532e of recess 524e; and an end of top magnet 304d rests on bottom surface 532g of recess 524g. As such, recesses 524a, 524c, 524e, and 524g are configured as top magnet mounting recesses. Recesses 524b, 524d, 524f, and 524h may be configured similarly to recesses 524a, 524c, 524e, and 524g, although in the illustrative embodiment, recesses 524b, 524d, 524f, and 524h do not receive a top magnet.

Adapter 308 may be configured to mount to bottom surface 404 of housing 300 of magnetic head 104. As shown in the illustrative embodiment, adapter 308 may be configured to snap fasten to bottom surface 404 of housing 300. With reference to FIG. 5C, side walls 528h of recess 524h extend above top surface 504 of adapter 308. Notches may be formed in side walls 528h to form a plurality of projections (one projection 536 of which is labeled) the plurality of projections configured to fit into recess 428h of bottom surface 404 of housing 300. Each projection of the plurality of projections has an outer surface (outer surface 540 is labeled) and a top end (top end 544 is labeled). Each projection of the plurality of projections may have a tab (tab 548 is labeled) mounted to extend outward from each respective outer surface near each respective top end. Each tab may be configured to fit into groove 444h of corresponding recess 428h of bottom surface 404 of housing 300 (see FIGS. 3B and 4A). With reference back to FIG. 5A, recesses 524a, 524c, and 524f of adapter plate 500 may be configured similarly to recess 524h. As such, recesses 524a, 524c, 524f, and 524h are configured to snap fasten to corresponding recesses 428a, 428c, 428f, and 428h of bottom surface 404 of housing 300.

Adapter 308 is configured to partially protrude into the menisci of liquid in the wells of sample plate 116 as adapter 308 translates over sample plate 116 in order to facilitate the collection of the plurality of magnetic particles as well as to facilitate the immersion and/or release of the magnetic particles into liquid in other wells of sample plate 116. As shown in the illustrative embodiment, bottom surface 508 of adapter plate 500 may be a curved surface which extends continuously along an entire length of bottom surface 508 between left side wall 516 and right side wall (not shown).

Adapter 308 may include a first rail 548 extending from front wall 512 of adapter plate 500 and a second rail 552 extending from back wall 520 of adapter plate 500. First and second rails 548, 552 enable adapter 308 to sweep through the menisci of liquid in the wells of sample plate 116 and prevent carryover of liquid from well to well.

The configuration of adapter 308 is not limiting. Other configurations may be used. By way of illustration, any of the adapters of U.S. application Ser. No. 14/595,926, which is herein incorporated by reference in its entirety, may be used.

Other devices may be mounted to magnetic head 104 of sample processing system 100, including devices associated with liquid handling, e.g., a liquid handling head configured to perform aspiration and/or dispensation of liquid through a plurality of pipetting heads into or out of the wells of sample plate 116.

Figure 11A:
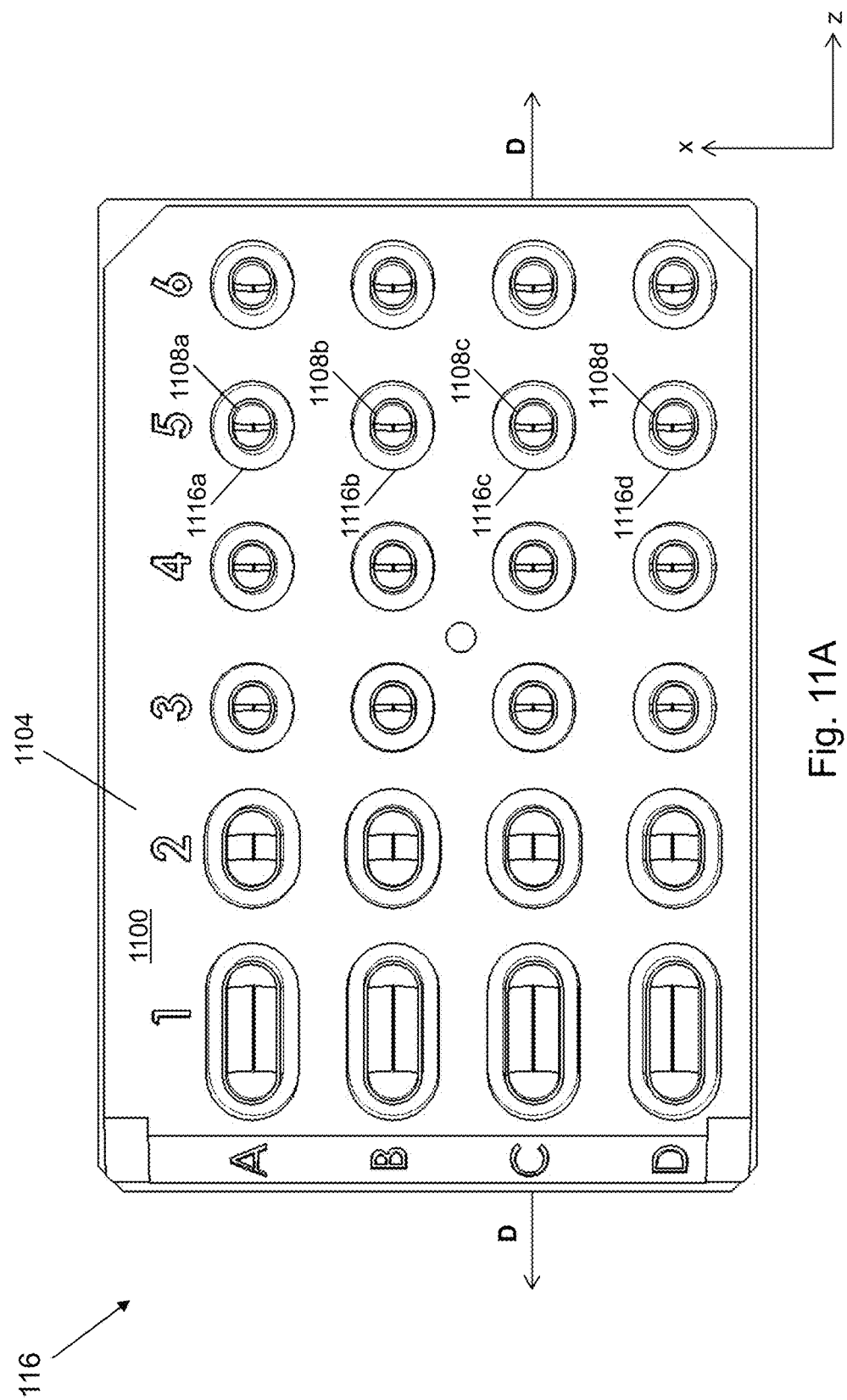
FIG. 11A depicts a top view of a sample plate of the sample processing system of FIG. 1.
Figure 11B:
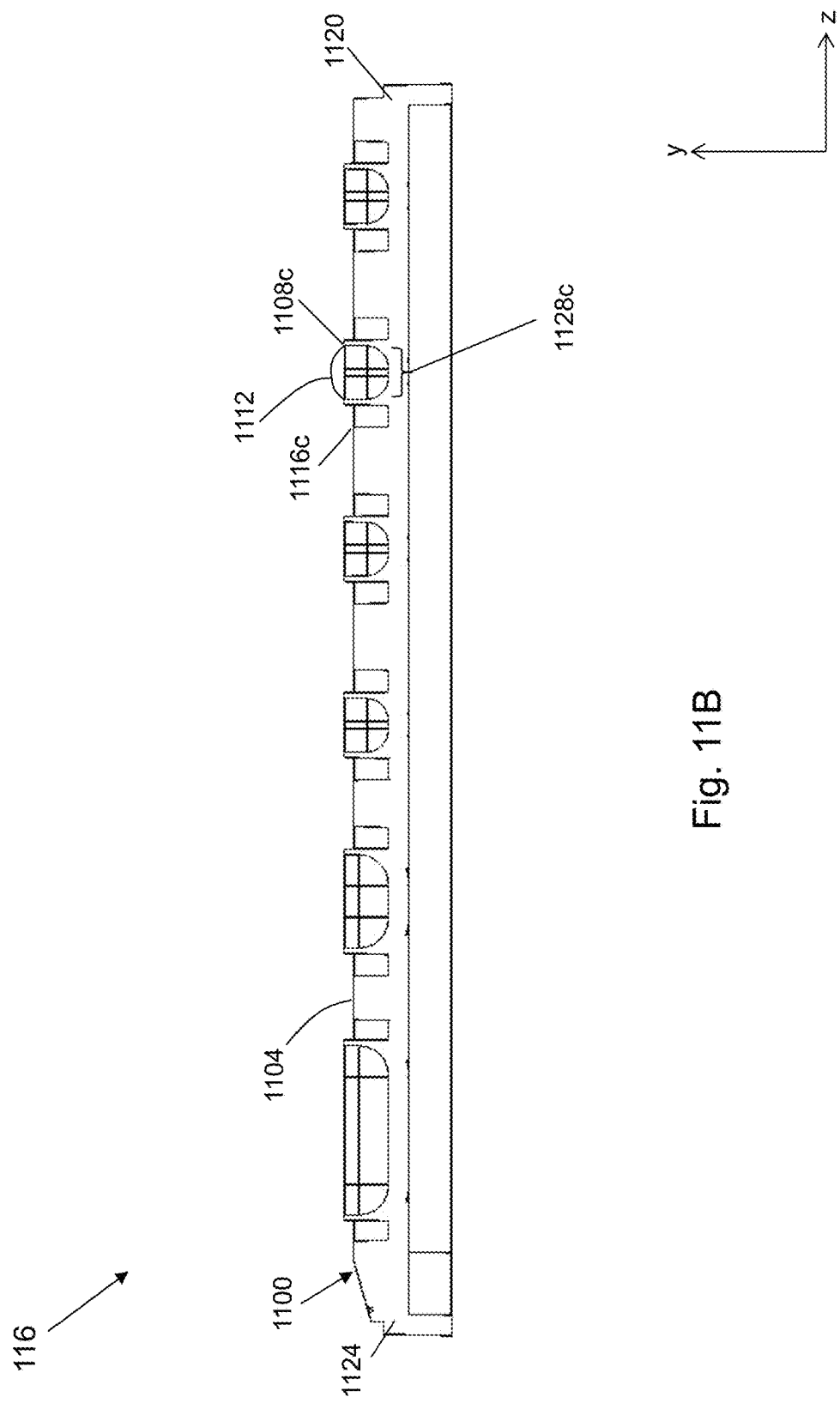
FIG. 11B depicts a left-side, cross-sectional view of the sample plate of FIG. 11A.

With reference to FIG. 11A-11B, views of sample plate 116 of sample processing system 100 are shown in accordance with an illustrative embodiment. FIG. 11A shows a top view of sample plate 116. FIG. 11B shows a left side, cross-sectional view of sample plate 116, taken along a section including axis D of FIG. 11A. Sample plate 116 is an illustrative embodiment of sample plate 208 of FIGS. 2A-2E. Sample plate 116 is configured to hold a plurality of liquid samples (e.g., liquid mixtures including target analytes bound to magnetic particles) and other liquid mixtures (e.g., liquid mixtures including processing reagents, buffers, wash solvents, etc.). Sample plate 116 may include a base plate 1100 having a top surface 1104 and a plurality of walls extending down from top surface 1104. A front wall 1120 and a back wall 1124 are labeled.

Base plate 1100 may include a plurality of wells, including wells 1108a-d formed in top surface 1104. The plurality of wells may be arranged in a grid pattern in top surface 1104, the grid pattern including rows of wells (rows are labeled A-D for illustration) and columns of wells (columns are labeled 1-6 for illustration). Each well of the plurality of wells is configured to hold a liquid having a meniscus protruding above top surface 1104. A meniscus 1112 of liquid contained in well 1108c is labeled. A bottom surface 1128c of well 1108c is also labeled. Base plate 1100 may include a plurality of reservoirs, including reservoirs 1116a-d formed in top surface, each reservoir surrounding a corresponding well in the plurality of wells. Each reservoir is configured to capture liquid spilling or wicking from a corresponding well.

The configuration of sample plate 116 and of each of the wells and each of the reservoirs is not limiting. Other configurations may be used. By way of illustration, any of the sample plates of U.S. application Ser. No. 14/595,985, which is herein incorporated by reference in its entirety, may be used.

Figure 6A:
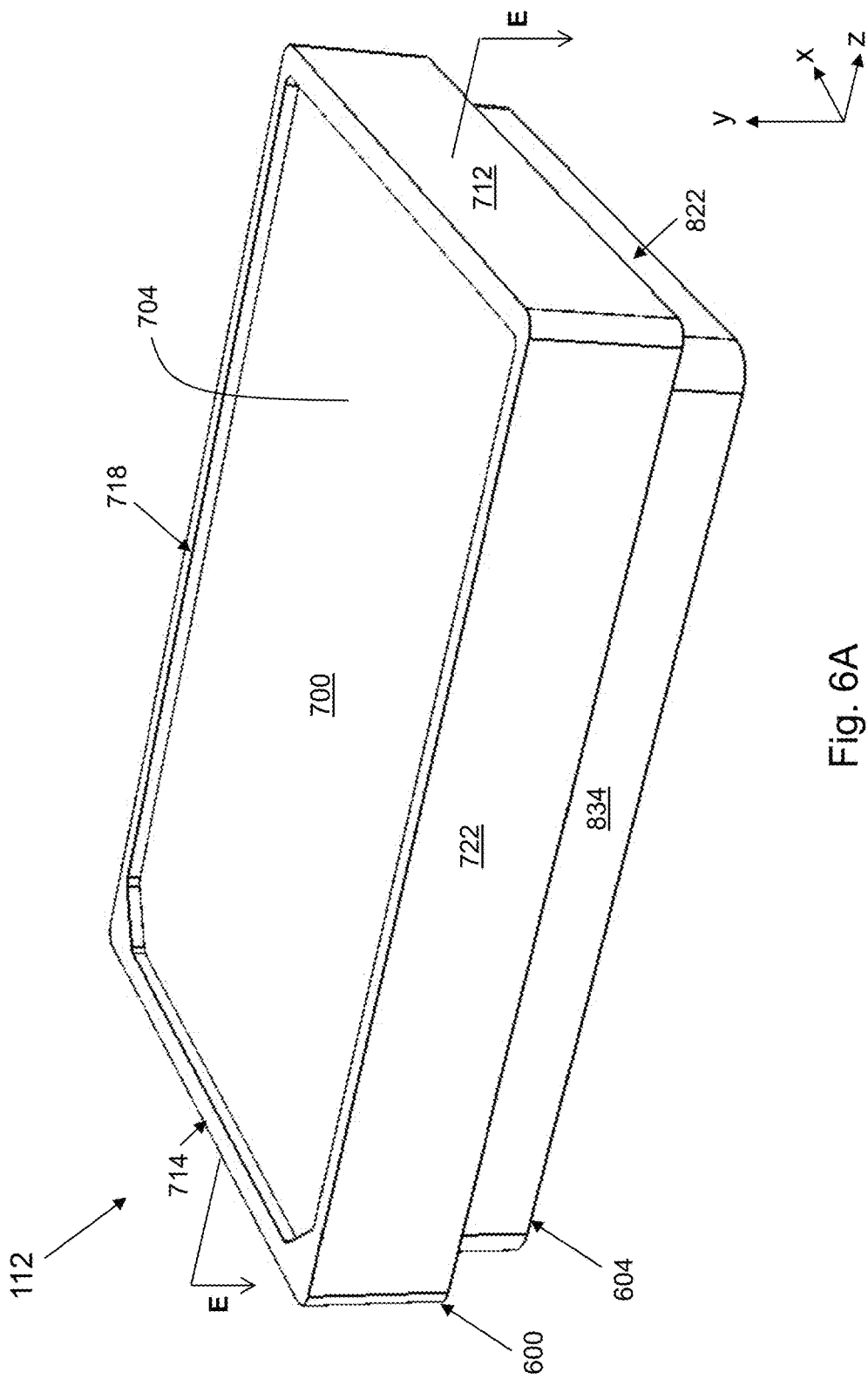
FIG. 6A depicts a perspective view of a magnetic base of the sample processing system of FIG. 1.
Figure 6B:
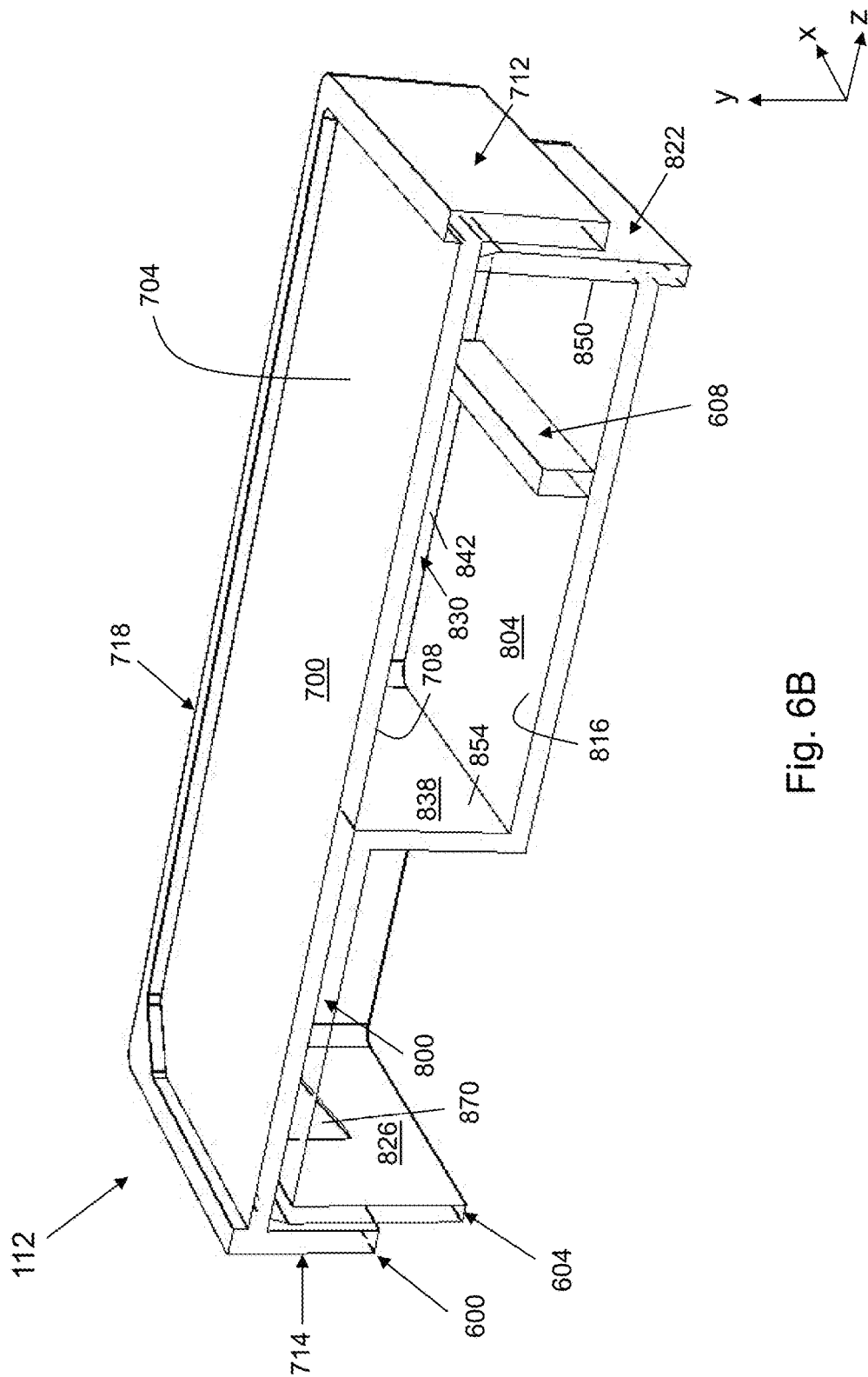
FIG. 6B depicts a perspective, cross-sectional view of the magnetic base of FIG. 6A.

With reference to FIGS. 6A-6B, views of magnetic base 112 of sample processing system 100 are shown in accordance with an illustrative embodiment. FIG. 6A shows a perspective view of magnetic base 112. FIG. 6B shows a perspective, cross-sectional view of magnetic base 112, taken along section E-E of FIG. 6A.

Magnetic base 112 is configured to mount to sample plate 116 (see FIG. 1 and FIGS. 12A-12C). Magnetic base 112 is also configured to accommodate bottom magnet 608 which provides a magnetic force for facilitating the release of the plurality of magnetic particles from adapter 308 of magnetic head 104 into liquid contained in wells of sample plate 116. Magnetic base 112 is an illustrative embodiment of magnetic base 220 of FIGS. 2A-2E. Magnetic base 112 may include a cover portion 600, a base portion 604, and bottom magnet 608. Magnetic base 112 may include fewer, additional, or different components.

Figure 7B:
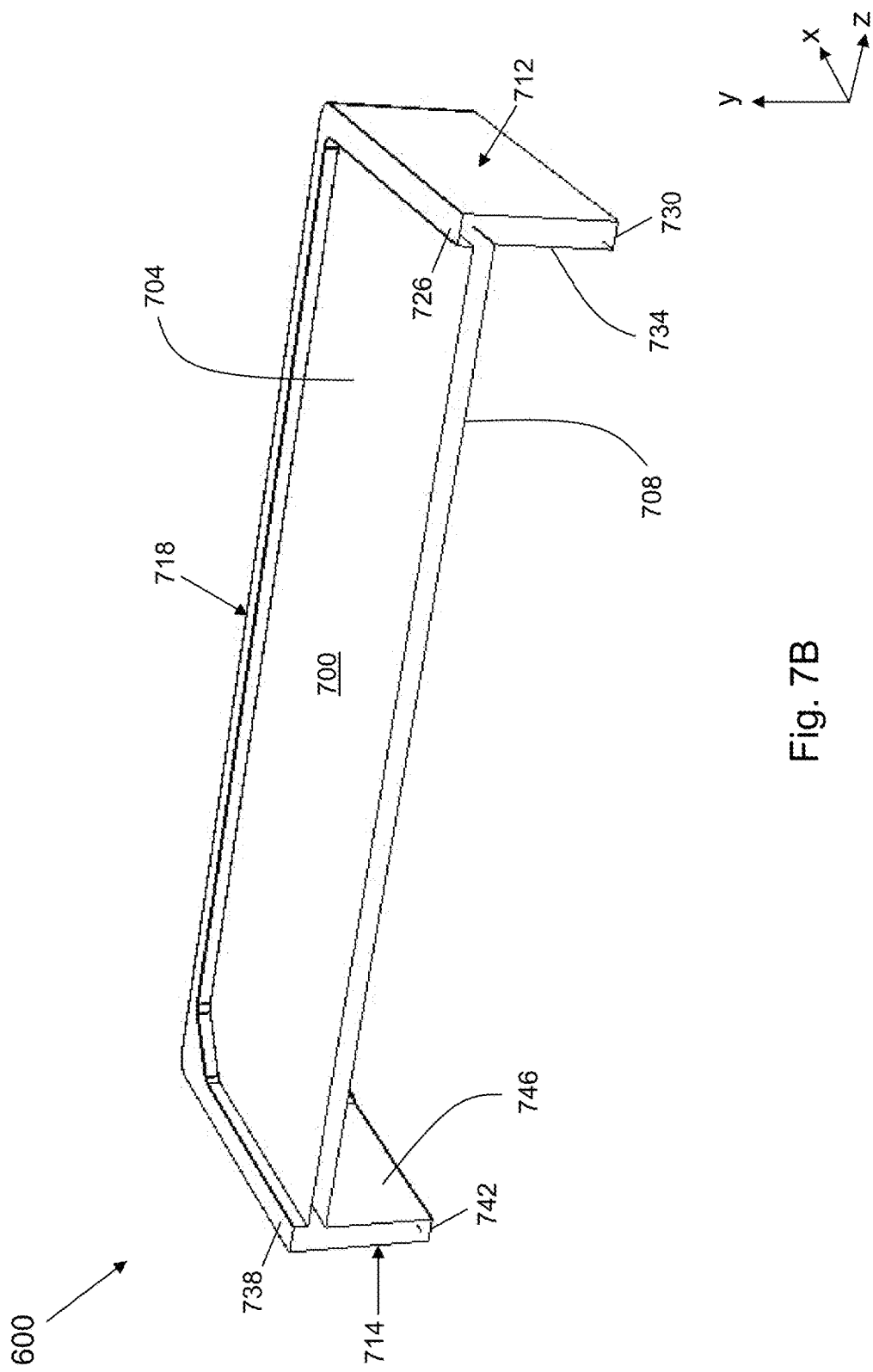
FIG. 7B depicts a perspective, cross-sectional view of the cover portion of FIG. 7A.

With reference to FIGS. 7A-7B, views of cover portion 600 of magnetic base 112 are shown. FIG. 7A shows a top view of cover portion 600. FIG. 7B shows a perspective, cross-sectional view of cover portion 600, taken along section E-E of FIG. 6A.

Cover portion 600 may include a cover plate 700 having a top surface 704 and a bottom surface 708. Cover portion 600 may further include a front wall 712, a back wall 714, a right side wall 718, and a left side wall 722 extending from cover plate 700. Each wall has a top end, a bottom end and an inner surface. A top end 726, a bottom end 730, and an inner surface 734 of front wall 712 are labeled in FIG. 7B. A top end 738, a bottom end 742, and an inner surface 746 of back wall 714 are also labeled in FIG. 7B. Cover plate 700 may be mounted to the inner surfaces of each of walls 712, 714, 718, 722 at a position which is below each top end of each wall but above each bottom end of each wall. In this way, top surface 704 of cover plate 700 and a portion of the inner surfaces of each of walls 712, 714, 718, 722 define surfaces of a top cavity configured to receive sample plate 116. Thus, the top cavity is configured as a sample plate mounting cavity. The size and shape of the top cavity, defined by cover plate 700 and walls 712, 714, 718, 722, may vary depending upon the size and shape of sample plate 116.

Similarly, bottom surface 708 of cover plate 700 and the inner surfaces of each of walls 712, 714, 718, 722 define surfaces of a bottom cavity configured to receive base portion 604 of magnetic base 112. Thus, the bottom cavity is configured as a base portion mounting cavity. The size and shape of the bottom cavity, defined by cover plate 700 and walls 712, 714, 718, 722, may also vary, depending upon the size and shape of base portion 604. The bottom cavity may be configured to at least partially enclose and cover base portion 604.

Figure 8A:
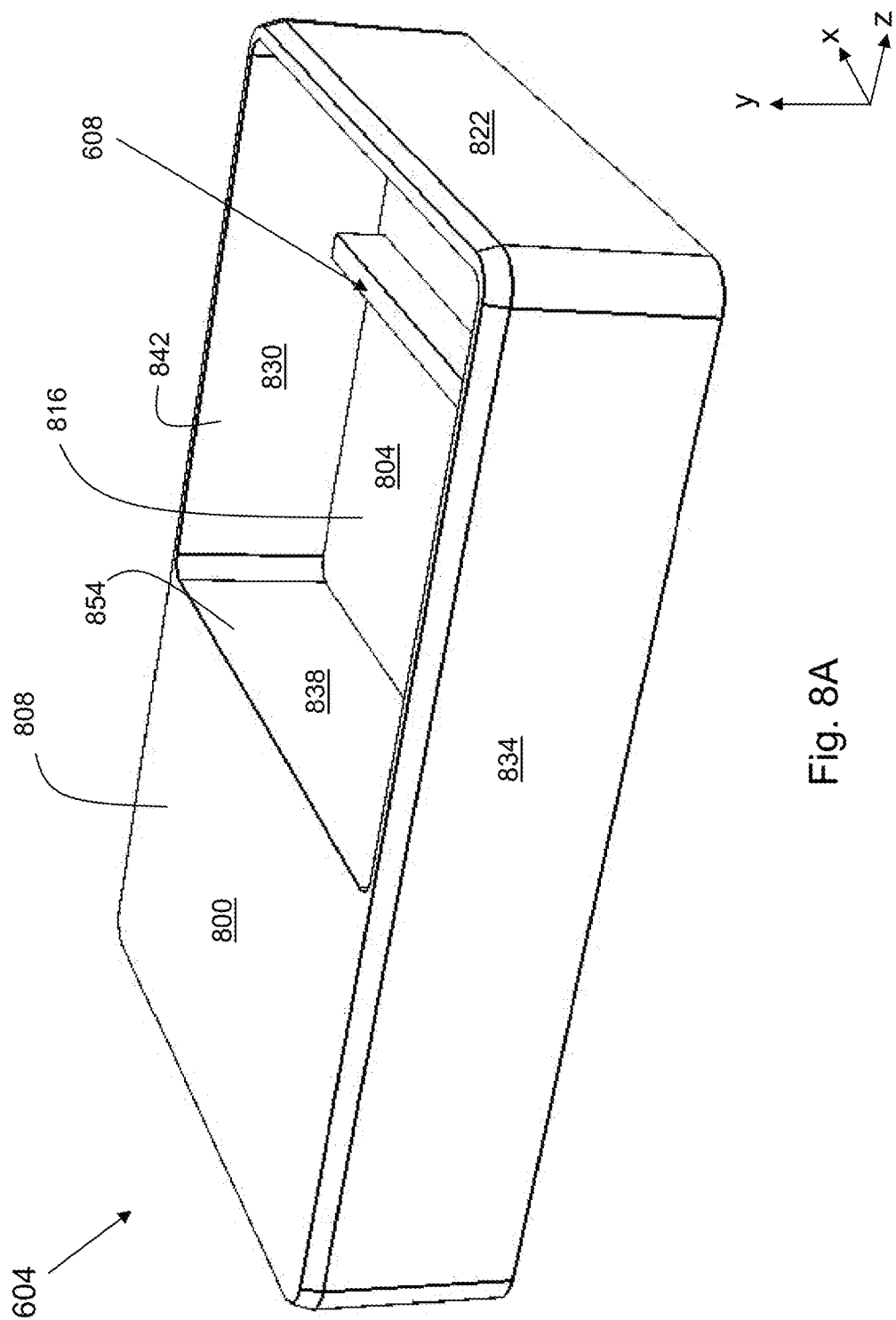
FIG. 8A depicts a perspective view of a base portion of the magnetic base of FIG. 6A.
Figure 8B:
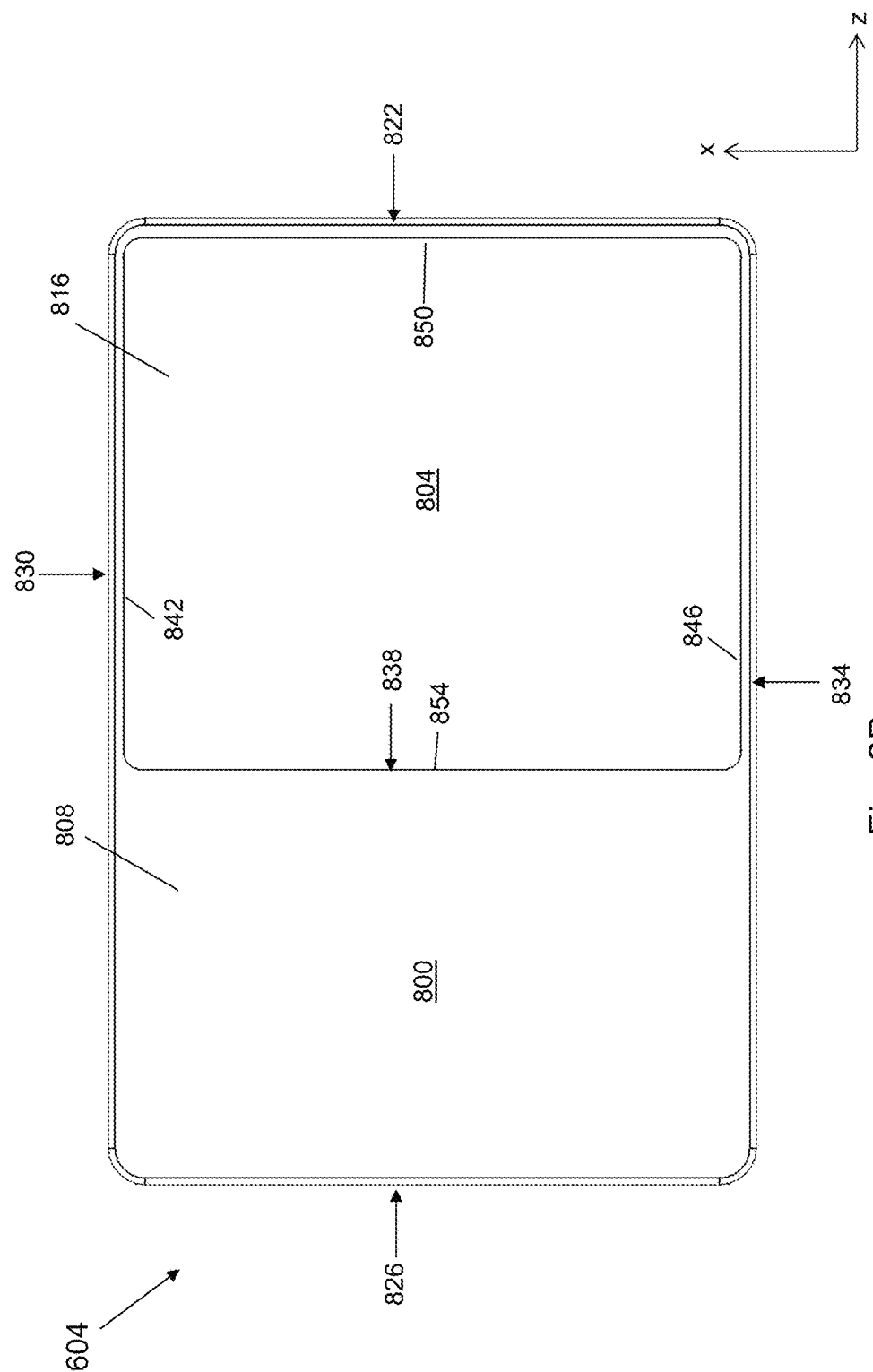
FIG. 8B depicts a top view of the base portion of FIG. 8A.
Figure 8D:
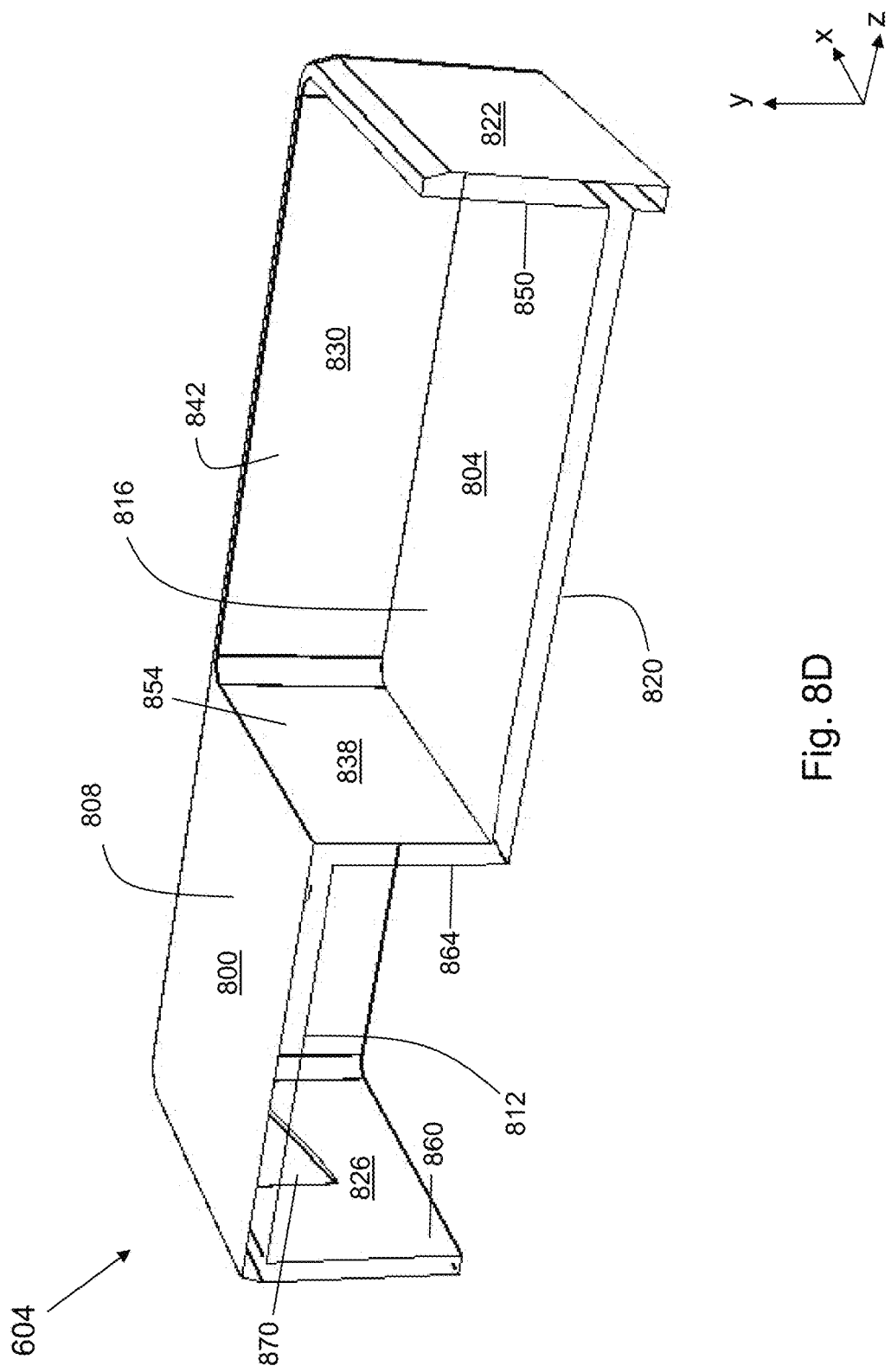
FIG. 8D depicts a perspective, cross-sectional view of the base portion of FIG. 8A.

With reference to FIGS. 8A-8D, views of base portion 604 of magnetic base 112 are shown. FIG. 8A shows a perspective view of base portion 604 (bottom magnet 608 is also shown). FIG. 8B shows a top view of base portion 604. FIG. 8C shows a bottom view of base portion 604. FIG. 8D shows a perspective, cross-sectional view of base portion 604, taken along section E-E of FIG. 6A.

Base portion 604 may include a top base plate 800 and a bottom base plate 804. Top base plate 800 has a top surface 808 and a bottom surface 812. Bottom base plate 804 also has a top surface 816 and a bottom surface 820. Base portion 604 may further include a front wall 822, a back wall 826, a right side wall 830, a left side wall 834, and an inner wall 838. Each wall has a top end, a bottom end and an inner surface. Inner wall 838 may be mounted to an inner surface 842 of right side wall 830 and an inner surface 846 of left side wall 834 such that inner wall 838 extends parallel to front wall 822 and back wall 826 and perpendicular to right side wall 830 and left side wall 834. Bottom base plate 804 may be mounted to an inner surface 850 of front wall 822, a first inner surface 854 of inner wall 838, inner surface 842 of right side wall 830, and inner surface 846 of left side wall 834. Bottom base plate 804 may be positioned at or near the bottom ends of walls 822, 838, 830, 834. In this way, top surface 816 of bottom base plate 804 and inner surfaces 850, 854, 842, 846 of walls 822, 838, 830, 834 (respectively) define surfaces of a base cavity configured to receive bottom magnet 608 (see also FIG. 6B). Thus, the base cavity is configured as a bottom magnet mounting cavity.

The size and shape of the bottom magnet mounting cavity, defined by bottom base plate 804 and walls 822, 838, 830, 834, may vary depending upon the size and shape of sample plate 116, including the number and arrangement of wells of sample plate 116. The dimension between right side wall 830 and left side wall 834 may be referred to as the width of the bottom magnet mounting cavity. The dimension between front wall 822 and inner wall 838 may be referred to as the length of the bottom magnet mounting cavity. The dimension between bottom base plate 804 and cover plate 700 (see FIG. 6B) may be referred to as the height of the bottom magnet mounting cavity.

Figure 12A:
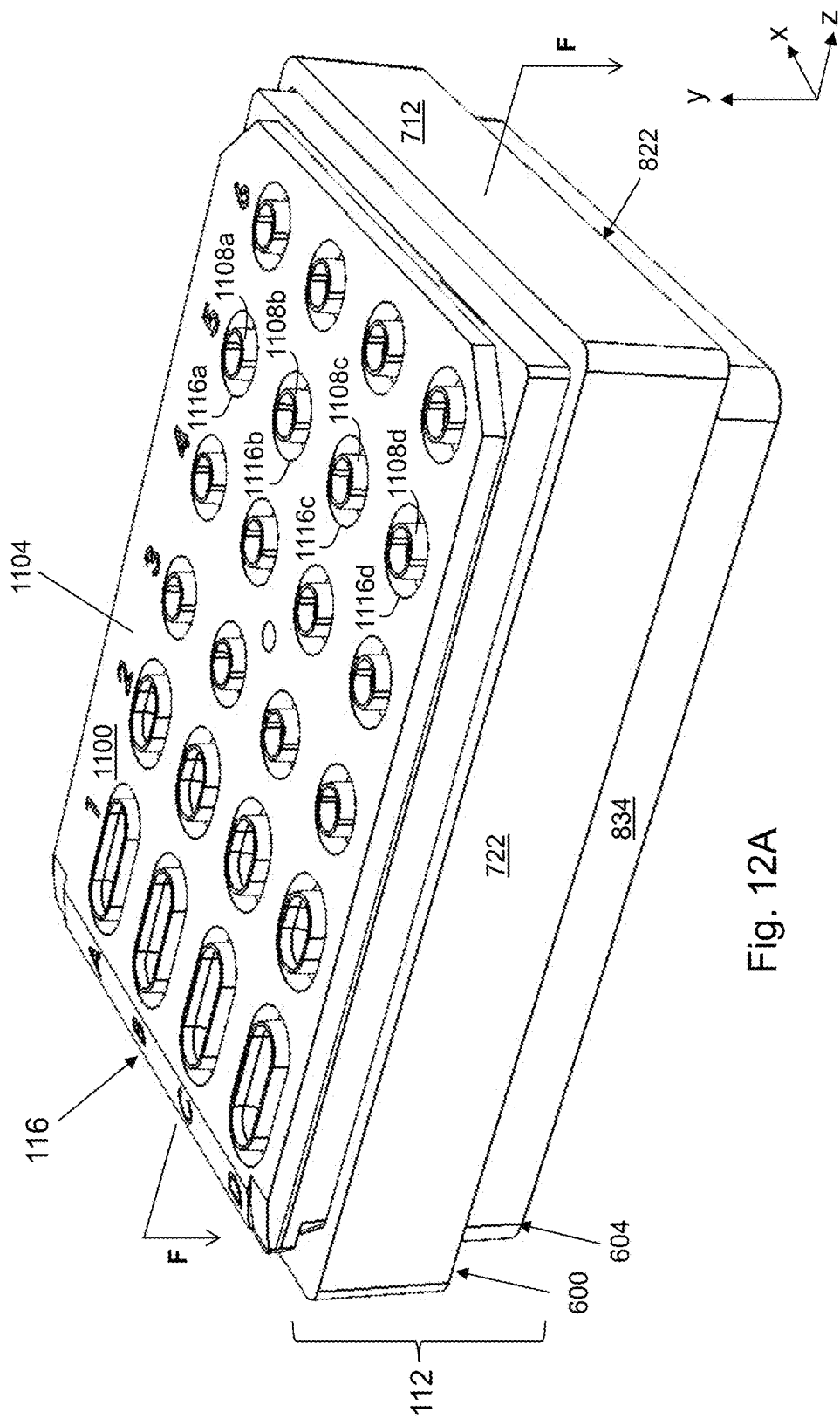
FIG. 12A depicts a perspective view of the sample plate of FIG. 11A mounted to the magnetic base of FIG. 6A.
Figure 12B:
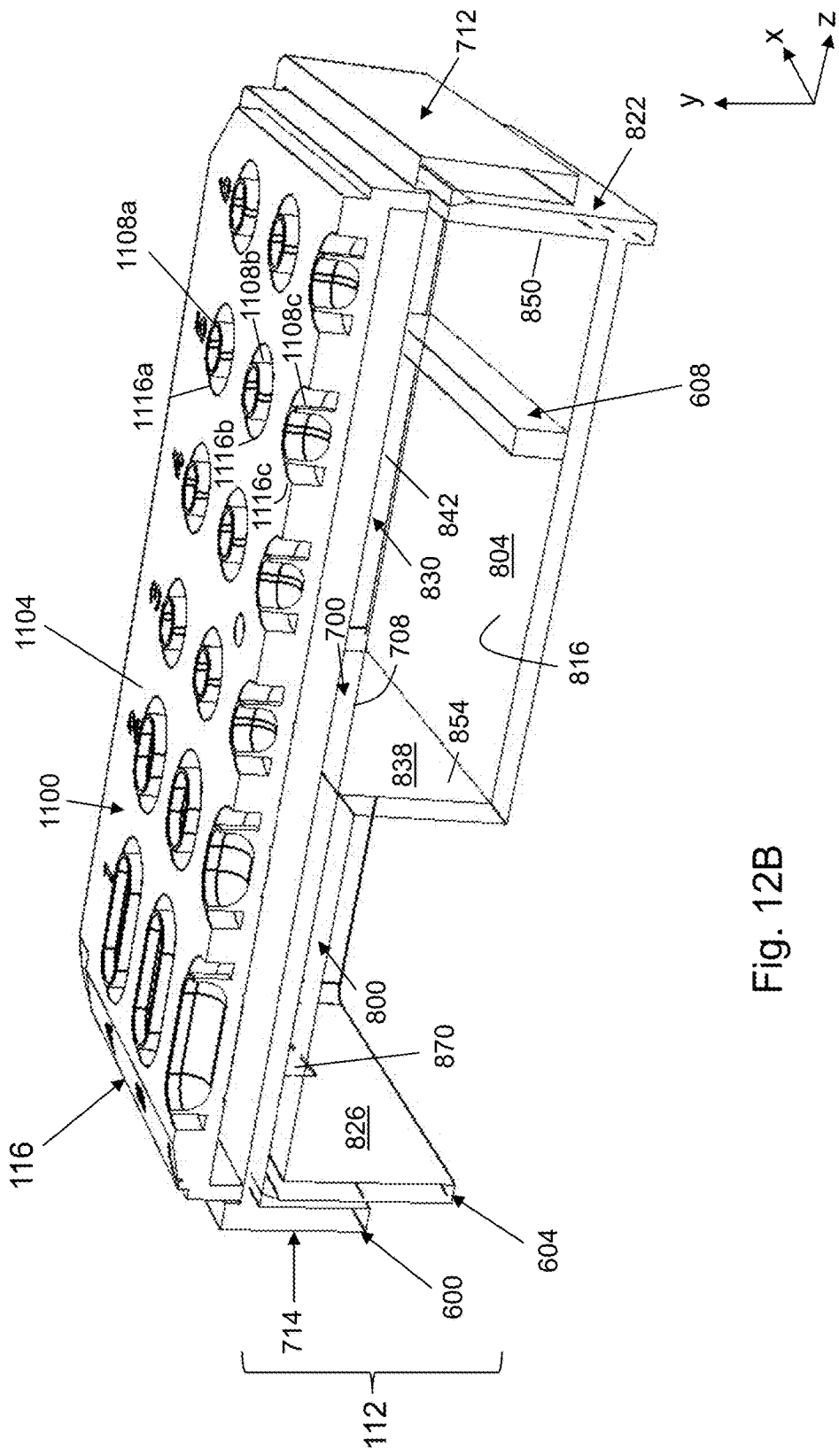
FIG. 12B depicts a perspective, cross-sectional view of FIG. 12A.
Figure 12C:
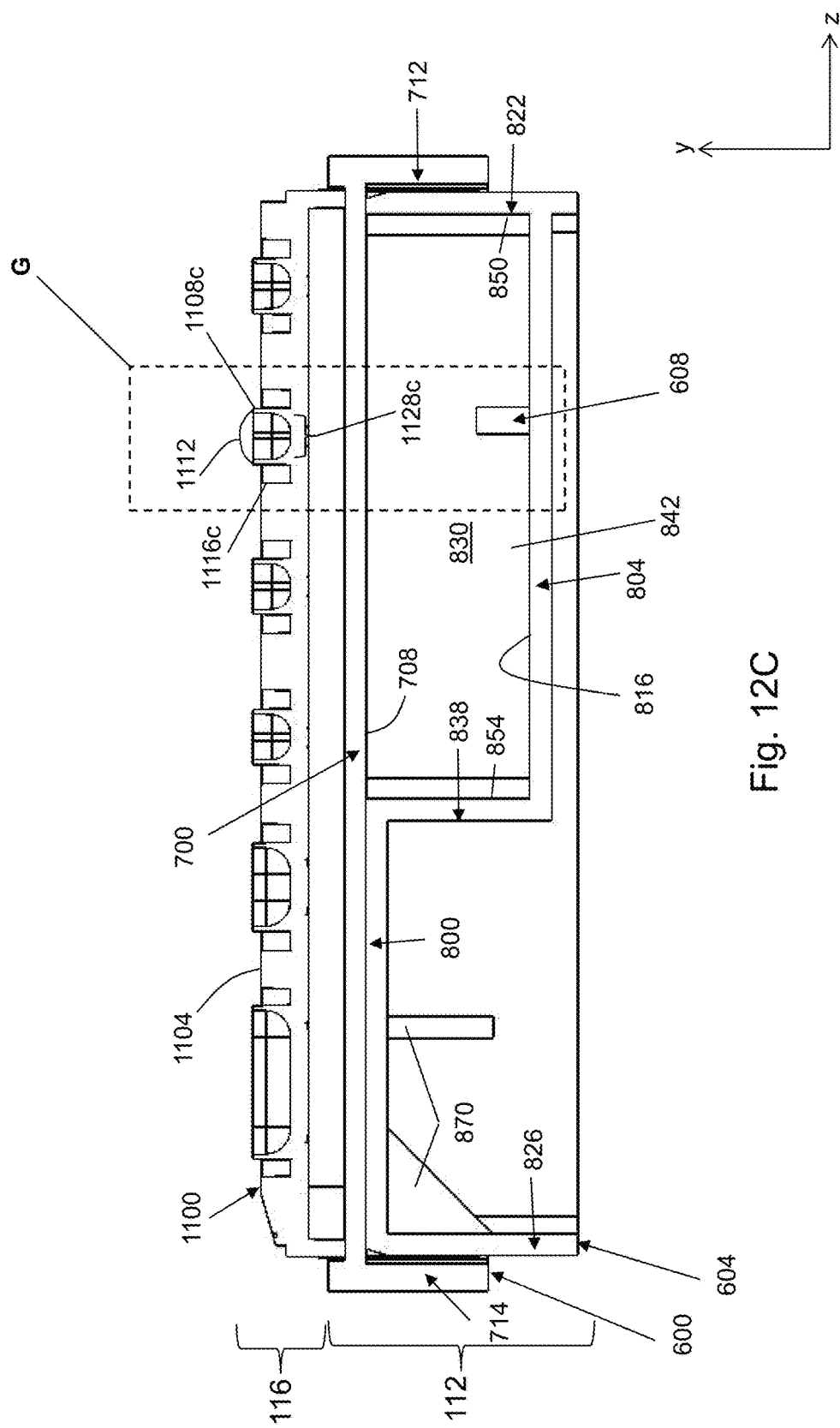
FIG. 12C depicts a left-side, cross-sectional view of FIG. 12A.

With reference to FIGS. 12A-12C, views of sample plate 116 mounted to magnetic base 112 are shown. FIG. 12A shows a perspective view. FIG. 12B shows a perspective, cross-sectional view, taken along section F-F of FIG. 12A. FIG. 12C shows a left side, cross-sectional view of section F-F of FIG. 12A. With reference to these figures, the length and width of the bottom magnet mounting cavity of base portion 604 defined by bottom base plate 804 and walls 822, 838, 830, 834 may be that which allows the bottom magnet mounting cavity to extend under a selected number of wells of sample plate 116, such that bottom magnet 608 may be used to facilitate the release of the plurality of magnetic particles into the liquid of the selected wells. By way of illustration, the length and width of the bottom magnet mounting may be selected such that the bottom magnet mounting cavity extends under each of the wells of columns 3, 4, 5 and 6. However, the length of the bottom magnet mounting cavity is such that bottom magnet mounting cavity does not extend under the wells of columns 1 and 2. In other words, the length of the bottom magnet mounting cavity is such that bottom magnet mounting cavity extends only under a subset of the wells of sample plate 116. Thus, in this illustrative embodiment, bottom magnet 608 cannot be used to facilitate the release of the plurality of magnetic particles into any of the wells of columns 1 and 2. However, this configuration is not limiting. The dimensions of the magnet mounting cavity may be such that the magnet mounting cavity extends under each of the wells of sample plate 116. In that case, it may not be necessary to include inner wall 838 or top base plate 800. In that case, bottom base plate 804 may extend to back wall 826.

Figure 9:
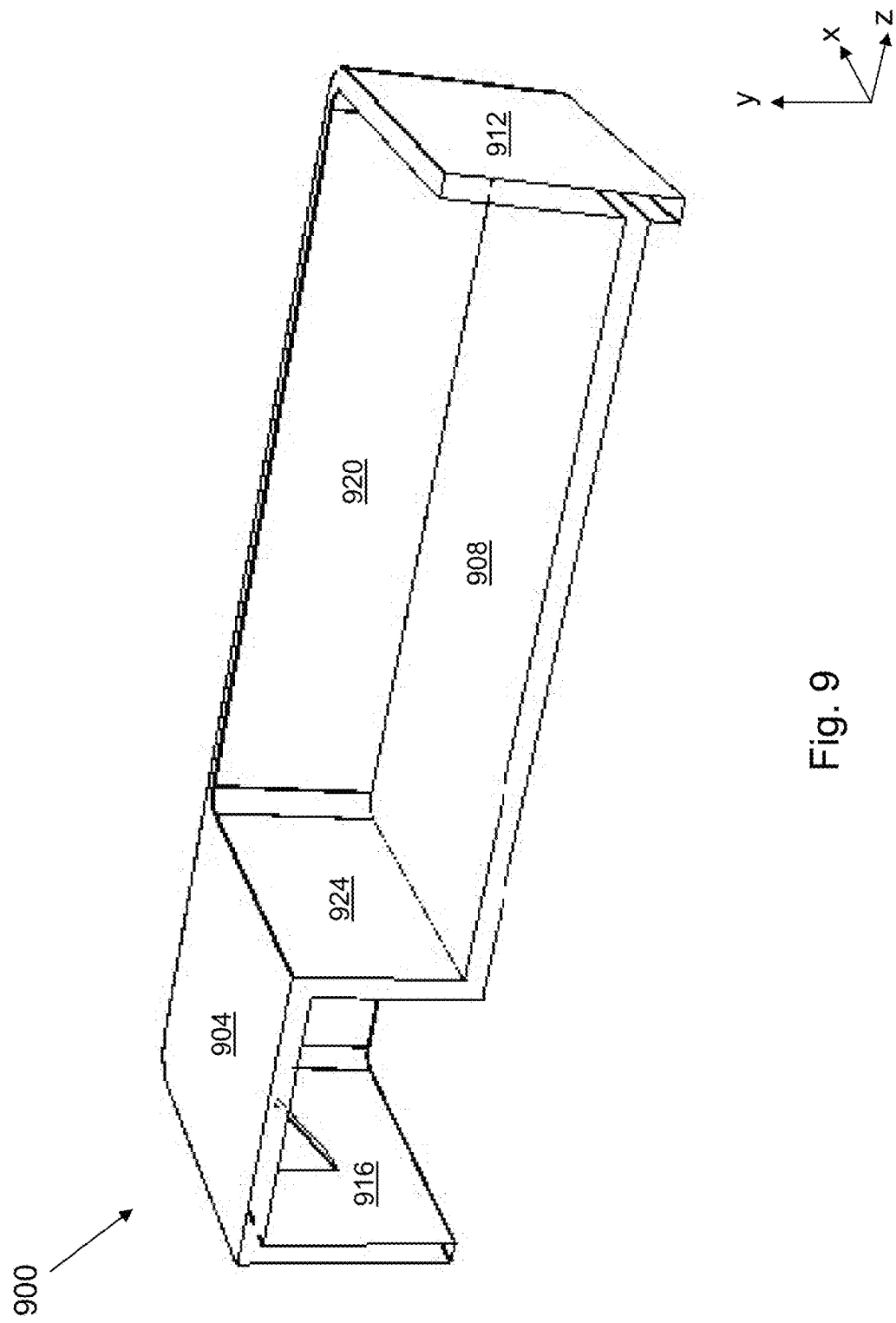
FIG. 9 depicts a perspective, cross-sectional view of a base portion in accordance with a second illustrative embodiment.

With reference to FIG. 9, a perspective, cross-sectional view of another illustrative base portion 900 for magnetic base 112 is shown. Base portion 900 may include a top base plate 904, a bottom base plate 908, a front wall 912, a back wall 916, a right side wall 920, a left side wall (not shown), and an inner wall 924. Bottom base plate 908 and walls 912, 924, 920 and the left side wall define a second bottom magnet mounting cavity. In this illustrative embodiment, the length of the second bottom magnet mounting cavity of base portion 900 is greater than the length of the bottom magnet mounting cavity of base portion 604 (see FIG. 8D). As such, the length and width of the bottom magnet mounting cavity of base portion 900 are that which allow the second bottom magnet mounting cavity to extend under an additional column of wells (column 2, with reference to FIG. 12A).

With reference back to FIGS. 8A-8D, top base plate 800 may be mounted to an inner surface 860 of back wall 826, a second inner surface 864 of inner wall 838, inner surface 842 of right side wall 830, and inner surface 846 of left side wall 834 at or near the top ends of walls 826, 838, 830, 834. Brackets 870 may be mounted to inner surfaces 860, 842, 846 of walls 826, 830, 834 (respectively) and to bottom surface 812 of top base plate 800 in order to support top base plate 800 and provide additional rigidity.

With reference back to FIGS. 6A-6B, when cover portion 600 is mounted to base portion 604, base portion 604 fits within the bottom cavity defined by cover plate 700 and walls 712, 714, 718, 722. In the illustrative embodiment, cover portion 600 partially encloses base portion 604 and entirely covers the bottom magnet mounting cavity defined by bottom base plate 804 and walls 822, 838, 830, 834. As such, cover plate 700 becomes a top of the bottom magnet mounting cavity, further defining the bottom magnet mounting cavity. As shown in FIG. 6B, a length of the sample plate mounting cavity defined by walls 712 and 714 is greater than the length of the bottom magnet mounting cavity defined by front wall 822 and inner wall 838. However, this configuration is not limiting.

Figure 10:
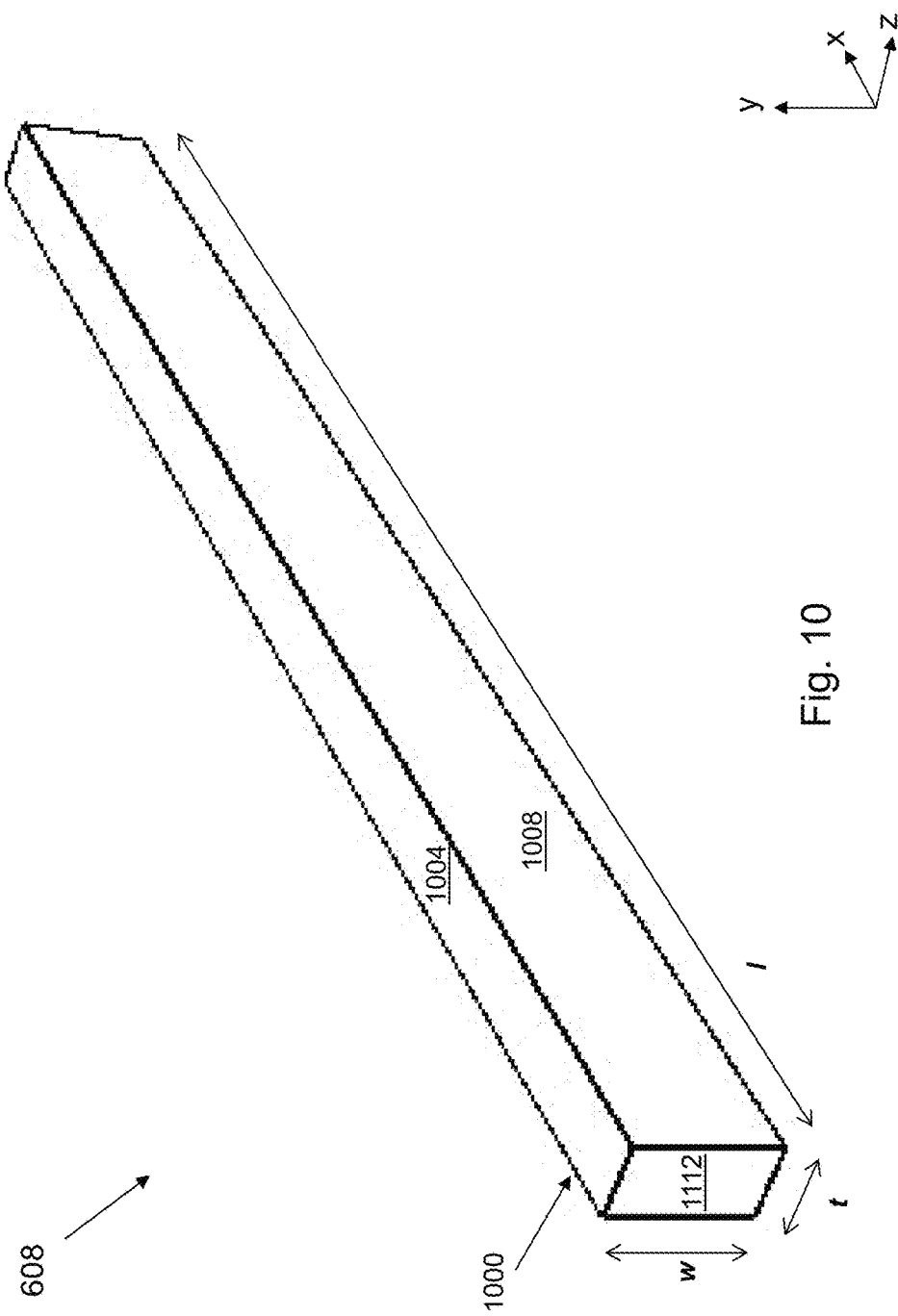
FIG. 10 depicts a perspective view of a bottom magnet of the magnetic base of FIG. 6A.

With reference to FIG. 10, a perspective view of bottom magnet 608. Bottom magnet 608 is an illustrative embodiment of bottom magnet 224 of FIGS. 2A-2E. Bottom magnet 608 is composed of a magnetic material (e.g., a permanent magnetic material). The magnetic material and the size and shape of bottom magnet 608 may be selected to produce a magnetic force sufficient to attract the plurality of magnetic particles in the liquid of a selected number of wells of sample plate 116 when bottom magnet 608 is in an upper position in the bottom magnet mounting cavity of base portion 604. Bottom magnet 608 may be configured as a bar 1000 having a top surface 1004, a bottom surface (not shown) opposite top surface 1004, a front surface 1008, a back surface (not shown) opposite front surface 1008, a right side surface (not shown) and a left side surface 1112 opposite the right side surface. The dimension between the right side surface and left side surface 1112 may be referred to as the length l. The dimension between top surface 1004 and the bottom surface may be referred to as the width w. The dimension between front surface 1008 and the back surface may be referred to as the thickness t. Bottom magnet 608 may be polarized across its width w, by which it is meant that its axis of magnetization is across its width w (see also FIGS. 2A-2E, showing bottom magnet 224 having an axis of magnetization across its width). Bottom magnet 608 may be oriented within the bottom magnet mounting cavity such that its length l extends parallel to front wall 822 and inner wall 838 of base portion 604 and perpendicular to the axis of translation of magnetic head 104 along the z-axis (see FIGS. 6B and 8A).

The length l, width w, and thickness t of bottom magnet 608 may vary. The length l may depend upon the size and shape of sample plate 116, including the number and arrangement of wells of sample plate 116. With reference to FIGS. 12A-12C, the length l may be selected such that bottom magnet 608 is sufficiently long to extend under a selected number of wells of sample plate 116 such that bottom magnet 608 may be used to facilitate the release of a plurality of magnetic particles into the liquid of the selected wells. By way of illustration, the length l of bottom magnet 608 may be sufficiently long to extend under each of the wells of a selected column of wells (e.g., column 5). The length l may be sufficiently long to extend from right side wall 830 to left side wall 834 of base portion 604 (see also FIG. 8A) of magnetic base 112. The thickness t of bottom magnet 608 may depend upon the size of the selected wells. With reference to FIG. 12C, the thickness t of bottom magnet 608 may be sufficient to extend across a bottom surface 1128c of well 1108c when bottom magnet 608 is centered underneath well 1108c. However, as shown in the illustrative embodiment, smaller thicknesses t may be used.

Bottom magnet 608 is a free floating magnet. By "free floating" it is meant that bottom magnet 608 is mounted within magnetic base 112 such that it is able to move substantially freely relative to the inner surfaces of the bottom magnet mounting cavity of base portion 604 of magnetic base 112. With reference to FIGS. 12A-12C, bottom magnet 608 is shown mounted within the bottom magnet mounting cavity defined by bottom base plate 804 and walls 822, 838, 830, 834. As shown in the illustrative embodiment, the bottom magnet mounting cavity does not include any mounting structure to restrict the movement of bottom magnet 608 along the x-axis, the y-axis, or the z-axis relative to the inner surfaces of the bottom magnet mounting cavity. Bottom magnet 608 is shown at rest on top surface 816 of bottom base plate 804 in a lower position within the bottom magnet mounting cavity. However, due to the absence of any mounting structure, bottom magnet 608 is able to move substantially freely relative to the inner surfaces of the bottom magnet mounting cavity (e.g., when under the influence of a magnetic force from the plurality of top magnets 304a-d of magnetic head 104).

By way of further illustration, when magnetic head 104 is appropriately positioned over sample plate 116 (e.g., each top magnet of the plurality of top magnets 304a-d centered over a respective well of a column of wells, adapter 308 in contact with liquid in each respective well, and each top magnet in its lower position), bottom magnet 608 is free to move upward in the direction of the y-axis to its upper position against bottom surface 708 of cover plate 700 due to the magnetic force from the plurality of top magnets 304a-d. Bottom magnet 608 is also free to translate along bottom surface 708 of cover plate 700 in the direction of the z-axis as magnetic head 104 translates across sample plate 116. The orientation of bottom magnet 608 while being held and translated is such that its polarity is aligned with (rather than opposite to) the polarity of the plurality of top magnets 304a-d. In the substantial absence of a magnetic force (e.g., when magnetic head 104 is no longer above sample plate 116), bottom magnet 608 is free to fall downward to again rest in its lower position on top surface 816 of bottom base plate 804. As illustrated in FIG. 13C, in the substantial absence of a magnetic force, bottom magnet 608 is also free to fall over onto front surface 1008 (see FIG. 10) or its back surface. In that case, the axis of magnetization of bottom magnet 608 is orthogonal to well 1108c. The polarization of bottom magnet 608 across its width w may facilitate this particular resting configuration of bottom magnet 608.

As shown in the illustrative embodiment, although no mounting structure in the bottom magnet mounting cavity restricts the movement of bottom magnet 608 along the x-axis, as described above, bottom magnet 608 may be sufficiently long to extend from right side wall 830 to left side wall 834 of base portion 604 of magnetic base 112 (see also FIG. 8A). Thus, in this configuration, the physical size of bottom magnet 608 limits the movement of bottom magnet 608 along the x-axis or the rotation of bottom magnet 608 about the y-axis. However, in this configuration, bottom magnet 608 may still be considered to be free floating.

As shown in the illustrative embodiment, cover portion 600 and base portion 604 of magnetic base 112 are separate components such that cover portion 600 may be removably mounted to base portion 604. Such a configuration facilitates access to bottom magnet 608. However, this configuration is not limiting.

Components of magnetic base 112 (other than bottom magnet 608) may be formed from a single piece of material. A variety of materials, e.g., plastic, may be used for the components of magnetic base 112 (other than bottom magnet 608). Bottom surface 708 of cover plate 700 may be made sufficiently smooth to facilitate translation of bottom magnet 608 across bottom surface 708 while bottom magnet 608 is being held by the magnetic force of the plurality of top magnets 304a-d of translating magnetic head 104.

Magnetic base 112 may include a plurality of bottom magnets mounted within the bottom magnet mounting cavity of base portion 604 to provide a similar effect and operation as described with respect to the single bottom magnet 608. By way of illustration only, a plurality of bottom magnets may be mounted in a holder and the holder mounted within the bottom magnet mounting cavity. The holder may be configured to mount the plurality of bottom magnets in a linear array, with each bottom magnet of the plurality of bottom magnets associated with a corresponding top magnet of the plurality of top magnets 304a-d. Various sizes and shapes may be used for each bottom magnet of the plurality of magnets as described with respect to bottom magnet 608. The holder may be oriented within the bottom magnet mounting cavity as described with respect to bottom magnet 608. The holder may be characterized by a length L, width W, and thickness T, which may be selected similarly as described with respect to the selection of the length l, width w, and thickness t of bottom magnet 608 relative to the configuration of the sample plate 116. In this embodiment, both the holder and the plurality of bottom magnets may be considered to be free floating, provided the holder (and thus the plurality of bottom magnets) are able to move substantially freely relative to the inner surfaces of the bottom magnet mounting cavity as described with respect to bottom magnet 608. Finally, in this embodiment, the material of the holder may physically separate the plurality of bottom magnets from the inner surfaces of the bottom magnet mounting cavity (e.g., if such material encloses or encases the plurality of bottom magnets). In such a configuration, the plurality of bottom magnets may still be considered to be held, resting, translating, etc. against the inner surfaces of the bottom magnet mounting cavity as described with respect to bottom magnet 608 even if they are not in direct physical contact with such inner surfaces due to the holder material.

Figure 13A:
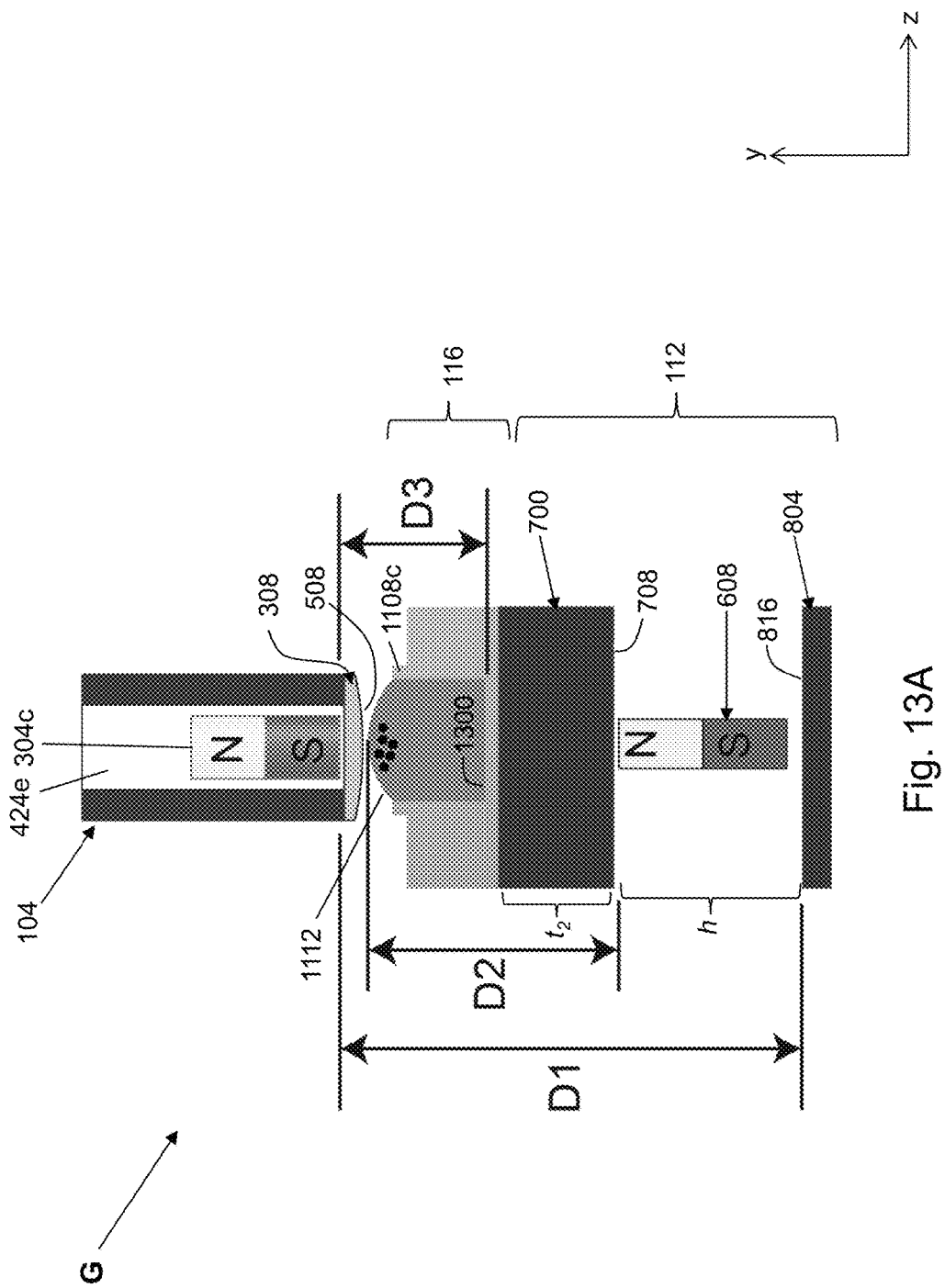
FIG. 13A depicts a schematic of a section of FIG. 12C in a first operational state (collect).
Figure 13B:
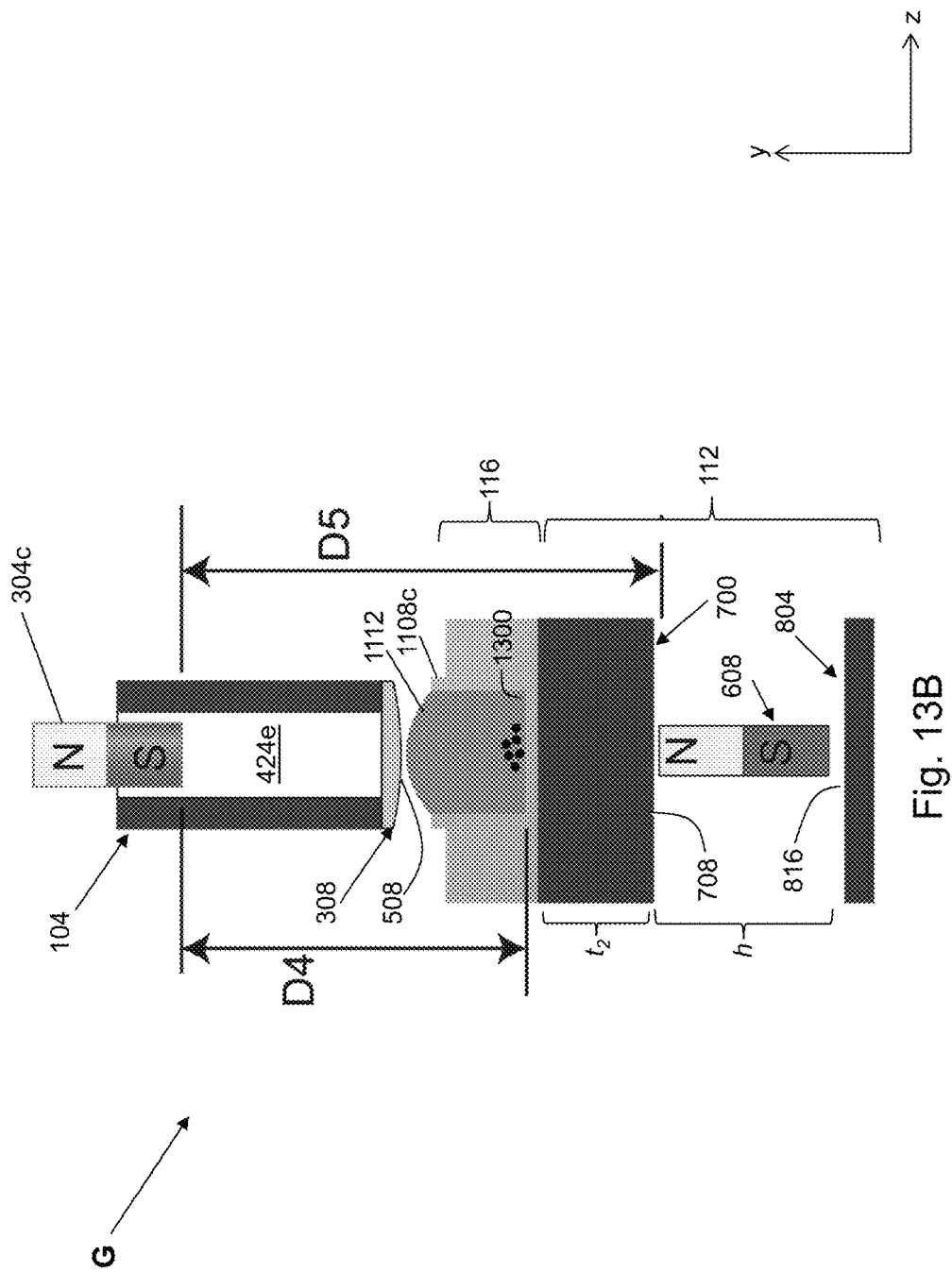
FIG. 13B depicts a schematic of a section of FIG. 12C in a second operational state (release).
Figure 13C:
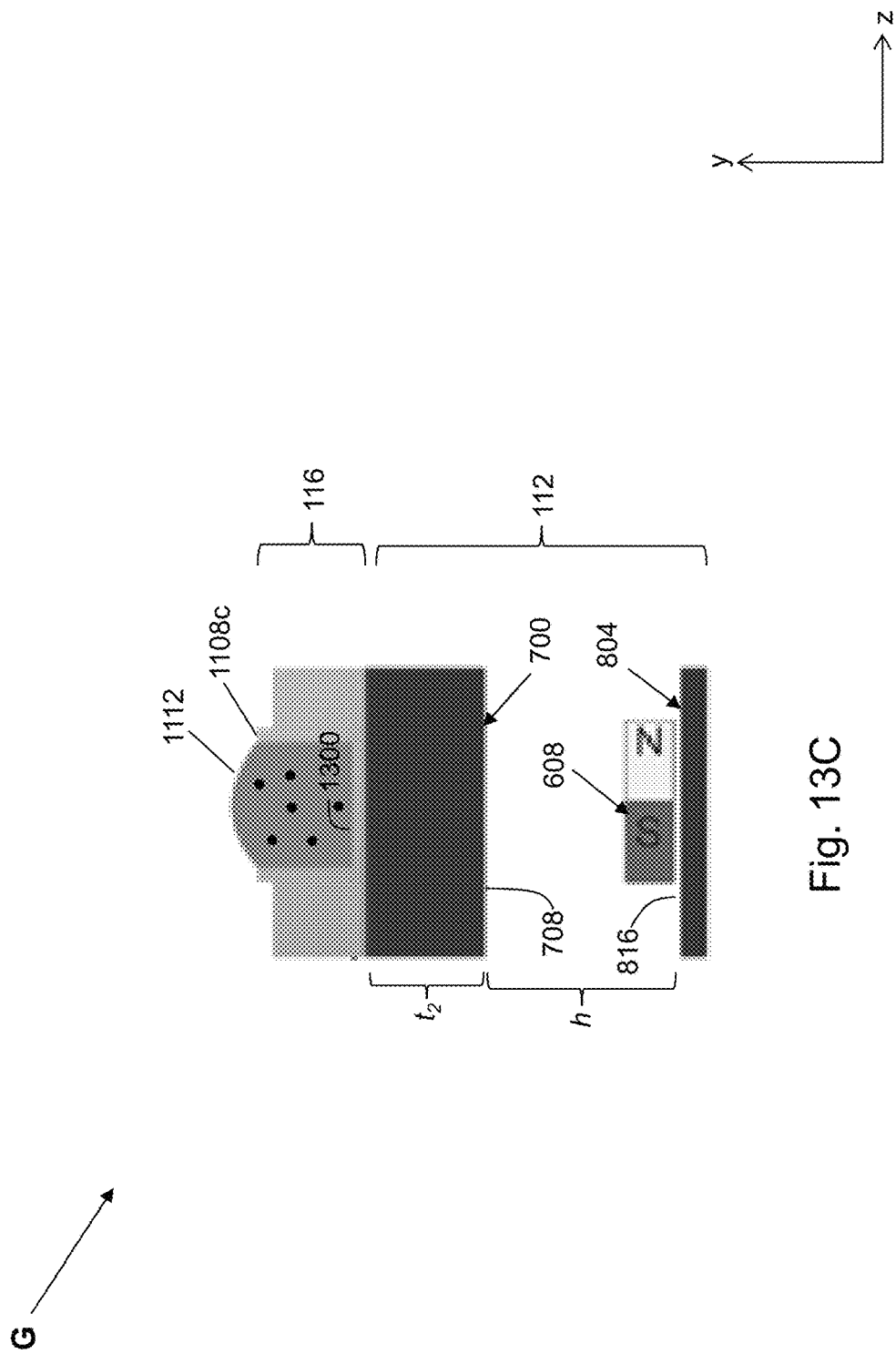
FIG. 13C depicts a schematic of a section of FIG. 12C in a third operational state (disperse).

With reference to FIGS. 13A-13C, views of a schematic of section G of FIG. 12C are shown. A schematic of magnetic head 104 is also shown in the views of FIGS. 13A-13B. The views of FIGS. 13A-13C correspond to a left side view of magnetic head 104, sample plate 116 and magnetic base 112. Magnetic head 104 includes top magnet 304c mounted in channel 424e and adapter 308 having bottom surface 508. Sample plate 116 includes well 1108c having bottom surface 1300. Liquid having meniscus 1112 in well 1108c includes a plurality of magnetic particles. Magnetic base 112 includes cover plate 700 having bottom surface 708, bottom base plate 804 having top surface 816, and bottom magnet 608. Bottom surface 708 and top surface 816 partially define the bottom magnet mounting cavity of magnetic base 112.

The views of FIGS. 13A-13C illustrate three operational states of sample processing system 100, collect (FIG. 13A), release (FIG. 13B), and disperse (FIG. 13C). In FIG. 13A (collect operational state), magnetic head 104 is centered over well 1108c and adapter 308 is in close proximity (e.g., in contact) with meniscus 1112 of liquid in well 1108c. Top magnet 304c is in its lower position within channel 424e, resting on bottom surface 532e of corresponding recess 524e of adapter 308 (see FIG. 3B). In this operational state, the plurality of magnetic particles is attracted to bottom surface 508 of adapter 308 due to the magnetic force from top magnet 304c, thereby collecting the plurality of magnetic particles on bottom surface 508 of adapter 308. Bottom magnet 608 is also attracted to bottom surface 708 of cover plate 700 due to the magnetic force from top magnet 304c such that bottom magnet 608 is held in its upper position within the bottom magnet mounting cavity of magnetic base 112 with its polarity aligned with the polarity of top magnet 304c. Bottom magnet 608 is also held in its upper position with this orientation relative to top magnet 304c during translation of magnetic head 104 along the z-axis.

In FIG. 13B (release operational state), magnetic head 104 remains centered over well 1108c (which may be another well of another column of wells of sample plate 116) and adapter 308 remains in contact with meniscus 1112. However, top magnet 304c is in its upper position within channel 424e. In this operational state, bottom magnet 608 remains held in its upper position to bottom surface 708 of cover plate 700 due to the magnetic force from top magnet 304c. However, the plurality of magnetic particles is now attracted to bottom surface 1300 of well 1108c due to the relatively closer proximity of bottom magnet 608 (and the magnetic force therefrom), thereby releasing the plurality of magnetic particles 1300 from bottom surface 508 of adapter 308.

In FIG. 13C (disperse operational state), magnetic head 104 (not shown) is translated beyond sample plate 116. In this operational state, bottom magnet 608 is free to fall back to its lower position on top surface 816 of bottom base plate 804 of magnetic base 112 where it exerts substantially no magnetic force of the plurality of magnetic particles 1300, thereby allowing the plurality of magnetic particles 1300 to disperse within the liquid in well 1108c.

The views of FIGS. 13A-13B also illustrate dimensions D1-D5 which may be selected to achieve the respective operational states. Dimension D1 is the dimension between a bottom surface of top magnet 304c and top surface 816 of bottom base plate 804 of magnetic base 112 as measured when top magnet 304c is in its lower position within channel 424e. Dimension D1 may be sufficiently small such that the magnetic force from top magnet 304c can move bottom magnet 608 from its lower position resting on top surface 816 of bottom base plate 804 to its upper position against bottom surface 708 of cover plate 700.

Dimension D2 is the dimension between bottom surface 508 of adapter 308 and bottom surface 708 of cover plate 700 of magnetic base 112. Dimension D3 is the dimension between the bottom surface of top magnet 304c and bottom surface 1300 of well 1108c as measured when top magnet 304c is in its lower position within channel 424e. Dimensions D2 and D3 may be sufficiently small such that the magnetic force from top magnet 304c can attract and collect the plurality of magnetic particles on bottom surface 508 of adapter 308. However, in the collect operational state, dimension D2 may be sufficiently large and greater than dimension D3 (i.e., D2>D3) such that the plurality of magnetic particles are attracted to bottom surface 508 of adapter 308 rather than to bottom surface 1300 of well 1108c due to the magnetic force from bottom magnet 608 when bottom magnet 608 is in its upper position.

Dimension D4 is the dimension between the bottom surface of top magnet 304c and bottom surface 1300 of well 1108c as measured when top magnet 304c is in its upper position within channel 424e. Dimension D4 may be sufficiently small such that the magnetic force from bottom magnet 608 can attract the plurality of magnetic particles to bottom surface 1300 of well 1108c. However, in the release operational state, dimension D4 may be greater than D2 (i.e., D4>D2) such that the plurality of magnetic particles are attracted to bottom surface 1300 of well 1108c rather than to bottom surface 508 of adapter 308 due to the magnetic force from top magnet 304c, thereby releasing the plurality of magnetic particles from bottom surface 508 of adapter 308.

Dimension D5 is the dimension between the bottom surface of top magnet 304c and bottom surface 708 of cover plate 700 of magnetic base 112 as measured when top magnet 304c is in its upper position within channel 424e. Dimension D5 may be sufficiently small such that the magnetic force from top magnet 304c can continue to attract and hold bottom magnet 608 in its upper position against bottom surface 708 of cover plate 700.

The stroke distance of top magnet 304c may be defined by D4–D3. The release operational state is achieved when the stroke distance is greater than the depth of the liquid in well 1108c. The depth of the liquid in well 1108c may be defined by D2–(D5–D4).

Dimensions D1-D5 may be selected to achieve the conditions described above, including by selecting an appropriate height h for the bottom magnet mounting cavity of magnetic base 112, and/or an appropriate thickness $t_2$ for cover plate 700, and/or an appropriate upper position of top magnet 304c (for a selected top magnet 304c, a selected bottom magnet 608, a selected sample plate 116 and a selected adapter 308). Similarly, an appropriate height h and/or an appropriate thickness $t_2$ may be selected to allow bottom magnet 608 to fall back to its lower position against top surface 816 of bottom base plate 804 in the substantial absence of the magnetic force from top magnet 304c such that bottom magnet 608 exerts substantially no magnetic force on the plurality of magnetic particles, thereby dispersing the plurality of magnetic particles within the liquid in well 1108c (for a selected bottom magnet 608).

Thus, dimensions (e.g., height h and thickness $t_2$) of the bottom magnet mounting cavity of magnetic base 112 may be selected to allow bottom magnet 608 to be moved to its upper position against bottom surface 708 of cover plate 700 by top magnet 304c when top magnet 304c is in its lower position within channel 424e and to collect the plurality of magnetic particles from well 1108c onto magnetic head 104. Such dimensions may further be selected to allow the plurality of magnetic particles to be attracted towards free floating magnet 608 in its upper position against bottom surface 708 of cover plate 700 when top magnet 304c is in its upper position within channel 424e so as to release the plurality of magnetic particles from magnetic head 104. Such dimensions may further be selected to allow free floating magnet 608 to fall back to its lower position against top surface 816 of bottom base plate 804 in the substantial absence of a magnetic force from top magnet 304c so as to disperse the plurality of magnetic particles within well 1108c. In other words, bottom magnet mounting cavity is configured to achieve such operational functions.

The benefits of automated sample processing system 100 including magnetic base 112 with free floating bottom magnet 608 include, but are not limited to, reduced complexity and cost savings. Drive system(s) are used to automatically control the movement of magnetic head 104 and the plurality of top magnets 304a-d relative to sample plate 116. The movement of the plurality of top magnets 304a-d is used to control the movement of bottom magnet 608. Thus, no separate drive system is required to reposition sample plate 116 or bottom magnet 608 relative to the plurality of top magnets 304a-d in order to facilitate the release of the plurality of magnetic particles from magnetic head 104.

Figure 14:
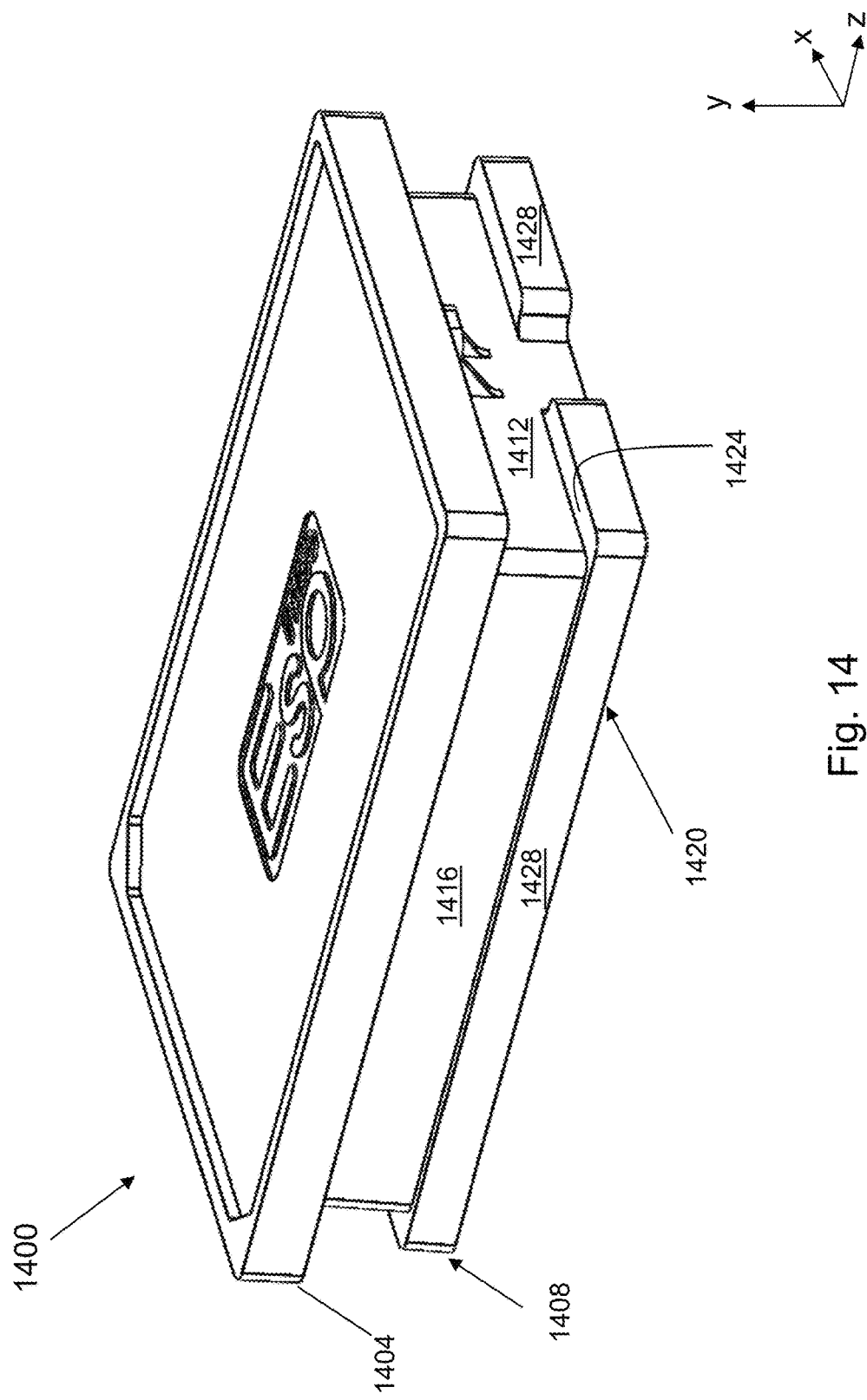
FIG. 14 depicts a perspective view of a magnetic base according to an illustrative embodiment.

With reference to FIG. 14, a perspective view of another illustrative magnetic base 1400 is shown. Magnetic base 1400 includes a cover portion 1404 and a base portion 1408. Base portion 1408 includes a front wall 1412, a back wall (not shown), a right side wall (not shown) and a left side wall 1416, each wall mounted to a bottom base plate (not shown). A ridge 1420 may be mounted to the outer surfaces of the walls at or near their ends. Ridge may have a top surface 1424 and side walls 1428. Ridge 1420 may or may not (as shown in FIG. 14) extend entirely around base portion 1404. Multiple notches may be defined in ridge 1420 such that ridge 1420 effectively is formed as a plurality of ridges. Ridge 1420 may be configured to facilitate the mounting of magnetic base 1400 to support plate 148 of work bed 132 of sample processing system 100 such that magnetic base 1400 may be securely and rigidly fixed in position during operation of sample processing system 100. This increases the precision and accuracy of the relative movements within the sample processing system 100 (e.g., the movement of magnetic head 104 and top magnets 304a-d relative to sample plate 116 mounted to magnetic base 1400). This also prevents top magnets 304a-d from pulling magnetic base 1400 off support plate 148 toward magnetic head 104. As such, ridge 1420 may have a shape and dimensions such that may fit within one of the cavities formed in support plate 148 and may be held in position via holder(s) (e.g., clips, thumbscrews, etc.) mounted to support plate 148 which can be pressed against top surface 1424 of ridge 1420.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the disclosure has been presented for purposes of illustration and of description. It is not intended to be exhaustive or to limit the disclosure to the precise form disclosed, and modifications and variations are possible in light of the above teachings or may be acquired from practice of the disclosure. The embodiments were chosen and described in order to explain the principles of the disclosure and as practical applications of the disclosure to enable one skilled in the art to utilize the disclosure in various embodiments and with various modifications as suited to the particular use contemplated. It is intended that the scope of the disclosure be defined by the claims appended hereto and their equivalents.

What is claimed is:

1. A magnetic base for a sample plate of a sample processing system, the magnetic base comprising:
   a first plate comprising
      a first top surface;
      a bottom surface; and
      a sample plate mounting cavity wall mounted to the first top surface, wherein the first plate and the sample plate mounting cavity wall define a sample plate mounting cavity configured to accommodate a sample plate of a sample processing system, the sample plate comprising a plurality of wells arranged parallel to the first plate; and
   a second plate extending parallel to the first plate, the second plate comprising
      a second top surface; and
      a magnet mounting cavity wall extending between the bottom surface of the first plate and the second top surface of the second plate, wherein the first plate, the second plate, and the magnet mounting cavity wall define a magnet mounting cavity comprising a free floating magnet wherein the dimensions of the magnet mounting cavity are such that the free floating magnet is able to translate within the magnet mounting cavity, relative to the first and second plates, in a direction parallel to the first and second plates, to be positioned directly under two or more wells of the plurality of wells.

2. The magnetic base of claim 1, wherein the magnet mounting cavity is configured to allow the free floating magnet to be moved to a first position against the bottom surface of the first plate by a top magnet of a magnetic head of the sample processing system when the top magnet is in a lower position relative to the first top surface of the first plate and to collect a plurality of magnetic particles from a well of the sample plate onto the magnetic head, wherein the magnet mounting cavity is configured to allow the plurality of magnetic particles to be attracted towards the free floating magnet in the first position against the bottom surface of the first plate when the top magnet is in an upper position relative to the first top surface of the first plate so as to release the plurality of magnetic particles from the magnetic head, and further wherein the magnet mounting cavity is configured to allow the free floating magnet to fall back to a second position against the second top surface of the second plate in the substantial absence of a magnetic force from the top magnet so as to disperse the plurality of magnetic particles within the well of the sample plate.

3. The magnetic base of claim 2, further wherein the magnet mounting cavity is configured to allow the free floating magnet to be translated along the bottom surface of the first plate by the top magnet in the lower position as the magnetic head is translated across the sample plate.

4. The magnetic base of claim 1, wherein the magnet mounting cavity does not comprise a mounting structure configured to mount the free floating magnet to a surface of the magnet mounting cavity and to restrict the movement of the free floating magnet relative to the surface of the magnet mounting cavity.

5. The magnetic base of claim 1, wherein the dimensions of the magnet mounting cavity are such that the magnet mounting cavity extends only under a subset of wells of a plurality of wells of the sample plate when mounted to the sample plate mounting cavity.

6. The magnetic base of claim 1, the first plate further comprising a plurality of sample plate mounting cavity walls mounted to the first top surface and defining the sample plate mounting cavity, wherein the sample plate mounting cavity wall is one of the plurality of sample plate mounting cavity walls, and the second plate further comprising a plurality of magnet mounting cavity walls extending between the bottom surface of the first plate and the second top surface of the second plate and defining the magnet mounting cavity, wherein the magnet mounting cavity wall is one of the plurality of magnet mounting cavity walls.

7. The magnetic base of claim 6, wherein the sample plate mounting cavity has a length defined by a front sample plate mounting cavity wall and an oppositely facing back sample plate mounting cavity wall, wherein the front and the back sample plate mounting cavity walls are ones of the plurality of sample plate mounting cavity walls, and further wherein the magnet mounting cavity has a length defined by a front magnet mounting cavity wall and an oppositely facing back magnet mounting cavity wall, wherein the front and back magnet mounting cavity walls are ones of the plurality of magnet mounting cavity walls.

8. The magnetic base of claim 7, wherein the length of the sample plate mounting cavity is greater than the length of the magnet mounting cavity.

9. The magnetic base of claim 1, wherein the free floating magnet is configured as a bar having a length, a width, and a thickness.

10. The magnetic base of claim 9, wherein the free floating magnet is polarized across its width.

11. The magnetic base of claim 1, the second plate further comprising a front magnet mounting cavity wall, a back magnet mounting cavity wall oppositely facing the front magnet mounting cavity wall, a first side magnet mounting cavity wall, and a second side magnet mounting cavity wall oppositely facing the first side magnet mounting cavity wall, each magnet mounting wall extending between the bottom surface of the first plate and the second top surface of the second plate and defining the magnet mounting cavity, wherein the magnet mounting cavity wall is one of the front, back, first side, and second side magnet mounting walls.

12. The magnetic base of claim 11, wherein the free floating magnet is configured as a bar having a length, a width, and a thickness.

13. The magnetic base of claim 12, wherein the length of the free floating magnet substantially extends from the first side magnet mounting cavity wall to the second side magnet mounting cavity wall.

14. The magnetic base of claim 1, further comprising a plurality of free floating magnets mounted within the magnet mounting cavity, wherein the free floating magnet is one of the plurality of free floating magnets.

15. The magnetic base of claim 14, wherein the free floating magnets of the plurality of free floating magnets are arranged in a linear array.

16. The magnetic base of claim 1, further comprising a cover portion comprising the first plate and the sample plate mounting cavity wall and a base portion comprising the second plate and the magnet mounting wall, wherein the cover portion is removably mounted to the base portion.

17. A sample processing system comprising:
a base comprising an upper surface;
a magnetic base mounted to the upper surface, the magnetic base comprising
a first plate comprising
a first top surface;
a bottom surface; and
a sample plate mounting cavity wall mounted to the first top surface, wherein the first plate and the sample plate mounting cavity wall define a sample plate mounting cavity configured to accommodate a sample plate of the sample processing system; and
a second plate extending parallel to the first plate, the second plate comprising
a second top surface; and
a magnet mounting cavity wall extending between the bottom surface of the first plate and the second top surface of the second plate, wherein the first plate, the second plate, and the magnet mounting cavity wall define a magnet mounting cavity configured to accommodate a free floating magnet; and
the free floating magnet mounted within the magnet mounting cavity;
the sample plate mounted in the sample plate mounting cavity, the sample plate comprising a plurality of wells; and
a magnetic head mounted to the base to translate over the sample plate in a translation direction, the magnetic head comprising a housing comprising a channel, a top magnet mounted in the channel such that the top magnet is movable within the channel between an upper position and a lower position relative to the first top surface of the first plate.

18. The sample processing system of claim 17, wherein the magnet mounting cavity is configured to allow the free floating magnet to be moved to a first position against the bottom surface of the first plate by the top magnet when the top magnet is in the lower position and to collect a plurality of magnetic particles from a well of the plurality of wells onto the magnetic head, wherein the magnet mounting cavity is configured to allow the plurality of magnetic particles to be attracted towards the free floating magnet in the first position against the bottom surface of the first plate when the top magnet is in the upper position so as to release the plurality of magnetic particles from the magnetic head, and further wherein the magnet mounting cavity is configured to allow the free floating magnet to fall back to a second position against the second top surface of the second plate in the substantial absence of a magnetic force from the top magnet so as to disperse the plurality of magnetic particles within the well of the plurality of wells.

19. The sample processing system of claim 18, further comprising a drive system configured to move the top magnet between the upper position and the lower position under electronic controls automatically.

\* \* \* \* \*